US011684667B2

(12) United States Patent
Baker et al.

(10) Patent No.: US 11,684,667 B2
(45) Date of Patent: Jun. 27, 2023

(54) CORONAVIRUSES, VACCINES COMPRISING THE SAME, AND METHODS FOR PREVENTING DISEASE

(71) Applicant: LOYOLA UNIVERSITY CHICAGO, Maywood, IL (US)

(72) Inventors: Susan Baker, Elmhurst, IL (US); Xufang Deng, Lyons, IL (US)

(73) Assignee: LOYOLA UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 15/910,617

(22) Filed: Mar. 2, 2018

(65) Prior Publication Data

US 2018/0333482 A1 Nov. 22, 2018

Related U.S. Application Data

(60) Provisional application No. 62/466,779, filed on Mar. 3, 2017.

(51) Int. Cl.

| | |
|---|---|
| ***A61K 39/215*** | (2006.01) |
| ***A61P 31/14*** | (2006.01) |
| ***A61K 39/12*** | (2006.01) |
| ***C12N 9/16*** | (2006.01) |
| ***A61K 39/00*** | (2006.01) |

(52) U.S. Cl.

CPC ............ *A61K 39/215* (2013.01); *A61K 39/12* (2013.01); *A61P 31/14* (2018.01); *C12N 9/16* (2013.01); *A61K 2039/5254* (2013.01); *C12N 2770/20022* (2013.01); *C12N 2770/20034* (2013.01)

(58) Field of Classification Search

CPC .................. A61K 39/215; A61K 39/12; A61K 2039/5254; A61K 2039/525; A61P 31/14; C12N 9/16; C12N 2770/20022; C12N 2770/20034; C12N 7/00; C12N 9/127; C12N 2770/20021; C12Y 207/07048

See application file for complete search history.

(56) References Cited

U.S. PATENT DOCUMENTS

| | | | | |
|---|---|---|---|---|
| 7,320,857 B2 | 1/2008 | Zhao et al. | | |
| 7,452,542 B2 | 11/2008 | Denison | | |
| 2006/0039926 A1* | 2/2006 | Denison | C07K 14/005 | 424/221.1 |
| 2007/0286872 A1* | 12/2007 | Denison | A61K 39/215 | 424/204.1 |

FOREIGN PATENT DOCUMENTS

| | | |
|---|---|---|
| WO | 20160012793 | 1/2016 |

OTHER PUBLICATIONS

Baker S, Nielsen EM, Jukneliene D. Nsp15; endoribonuclease [Murine hepatitis virus strain JHM]. NCBI Reference Sequence: YP_209242.1. Dep. Feb. 22, 2005.*

Yong CY, Ong HK, Yeap SK, Ho KL, Tan WS. Recent Advances in the Vaccine Development Against Middle East Respiratory Syndrome—Coronavirus. Front Microbiol. Aug. 2, 2019;10:1781.*

Zheng A, Shi Y, Shen Z, Wang G, Shi J, Xiong Q, Fang L, Xiao S, Fu ZF, Peng G. Insight into the evolution of nidovirus endoribonuclease based on the finding that nsp15 from porcine Deltacoronavirus functions as a dimer. J Biol Chem. Aug. 3, 2018;293(31):12054-12067. Epub Jun. 10, 2018.*

Athmer J, Fehr AR, Grunewald M, Smith EC, Denison MR, Perlman S. In Situ Tagged nsp15 Reveals Interactions with Coronavirus Replication/Transcription Complex-Associated Proteins. mBio. Jan. 31, 2017;8(1).*

Kang H, Bhardwaj K, Li Y, Palaninathan S, Sacchettini J, Guarino L, Leibowitz JL, Kao CC. Biochemical and genetic analyses of murine hepatitis virus Nsp15 endoribonuclease. J Virol. Dec. 2007;81(24):13587-97. Epub Sep. 26, 2007.*

Bhardwaj K, Palaninathan S, Alcantara JM, Yi LL, Guarino L, Sacchettini JC, Kao CC. Structural and functional analyses of the severe acute respiratory syndrome coronavirus endoribonuclease Nsp15. J Biol Chem. Feb. 8, 2008;283(6):3655-64. Epub Nov. 28, 2007.*

Zuniga S, Pascual-Iglesias A, Sanchez CM, Sola I, Enjuanes L. Virulence factors in porcine coronaviruses and vaccine design. Virus Res. Dec. 2, 2016;226:142-151. Epub Jul. 7, 2016.*

Kindler E, Gil-Cruz C, Spanier J, Li Y, Wilhelm J, Rabouw HH, Züst R, Hwang M, V'kovski P, Stalder H, Marti S, Habjan M, Cervantes-Barragan L, Elliot R, et. al. Early endonuclease-mediated evasion of RNA sensing ensures efficient coronavirus replication. PLoS Pathog. Feb. 3, 2017;13(2):e1006195. (Year: 2017).*

Kang, H. et al., "Biochemical and genetic analyses of murine hepatitis virus Nsp15 endoribonuclease", Journal of Virology, Dec. 2007; vol. 81. No 24, pp. 13587-13597.

Athmer, J. et al., "In situ tagged nsp15 reveals interactions with coronavirus replication/transcription complex-associted proteins", mBio. Jan. 31, 2017, vol. 8, No. 1,e02320-16 (pp. 1-14).

International Search Report and Written Opinion dated Jun. 7, 2018 for PCT/US18/20678 filed Mar. 2, 2018.

Kindler E, Gil-Cruz C, Spanier J, Li Y, Wilhelm J, Rabouw HH, Züst R, Hwang M, V'kovski P, Stalder H, Marti S, Habjan M, Cervantes-Barragan L, Elliot R, Karl N, Gaughan C, van Kuppeveld FJ, Silverman RH, Keller M, Ludewig B, Bergmann CC, Ziebuhr J, Weiss SR, Kalinke U, Thiel V. Early endonuclease-mediated evasion of RNA sensing ensures efficient coronavirus replication. PLoS Pathog. Feb. 3, 2017;13(2) :e1006195.

Xufang Deng, Matthew Hackbart, Robert C. Mettelman, Amornrat O'Brien, Anna M. Mielech, Guanghui Yi, C. Cheng Kao, and Susan C. Baker; "Coronavirus nonstructural protein 15 mediates evasion of dsRNA sensors and limits apoptosis in macrophages", PNAS Plus Microbiology; Apr. 12, 2017.

* cited by examiner

*Primary Examiner* — Rachel B Gill

(74) *Attorney, Agent, or Firm* — Marshall, Gerstein & Borun LLP

(57) ABSTRACT

Coronaviruses, vaccines comprising the same, and methods for preventing disease. One embodiment of such includes a live, attenuated coronavirus comprising a variant replicase gene encoding polyproteins comprising a non-structural protein (nsp)-15, the replicase gene encoding the nsp15 and causes any change, including mutations and/or deletions, that affects the stability or activity of the nsp15.

4 Claims, 19 Drawing Sheets

Specification includes a Sequence Listing.

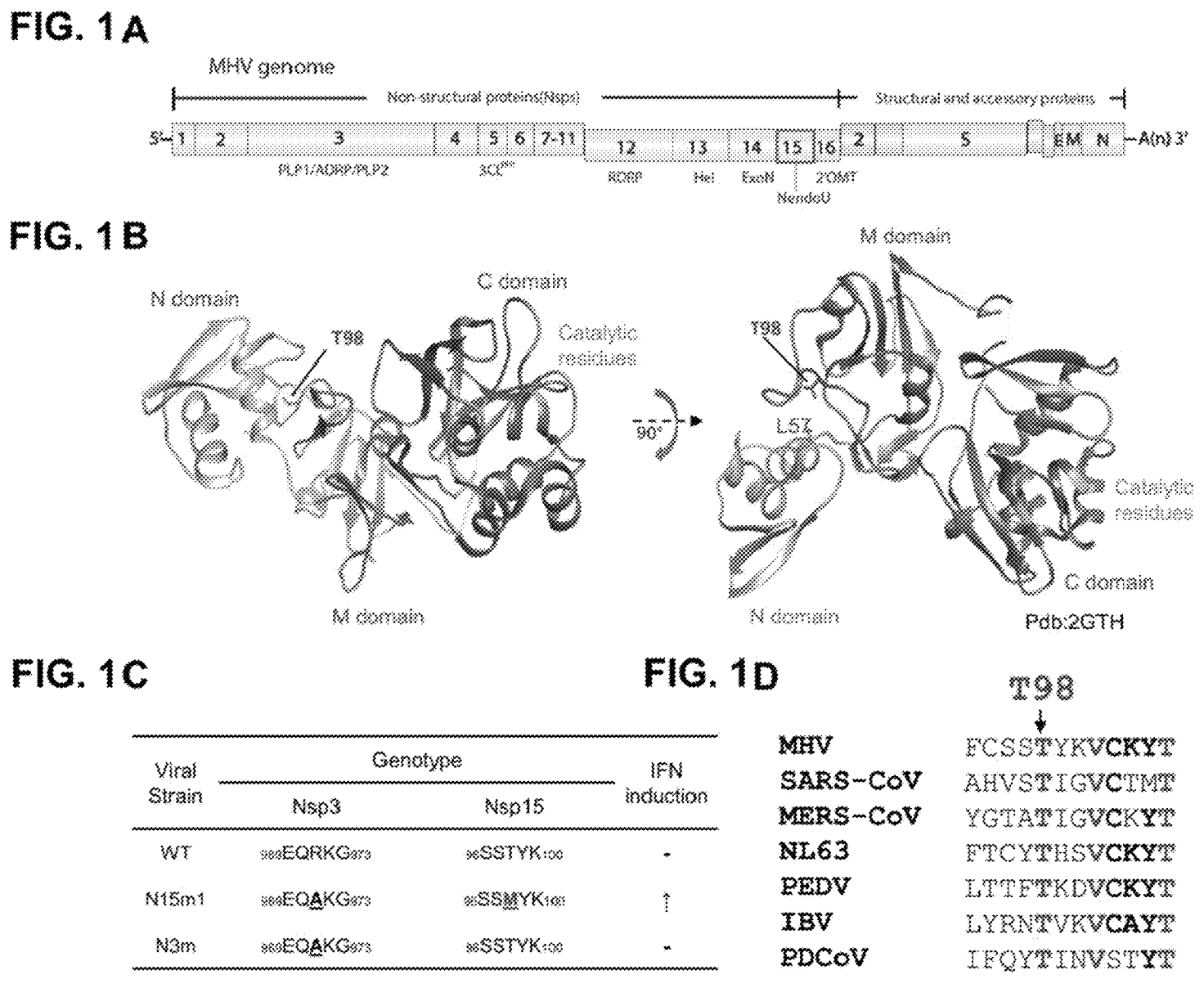

| Viral Strain | Genotype | | IFN induction |
|---|---|---|---|
| | Nsp3 | Nsp15 | |
| WT | $_{869}$EQRKG$_{873}$ | $_{96}$SSTYK$_{100}$ | - |
| N15m1 | $_{869}$EQAKG$_{873}$ | $_{96}$SSMYK$_{100}$ | ↑ |
| N3m | $_{869}$EQAKG$_{873}$ | $_{96}$SSTYK$_{100}$ | - |

FIG. 1D

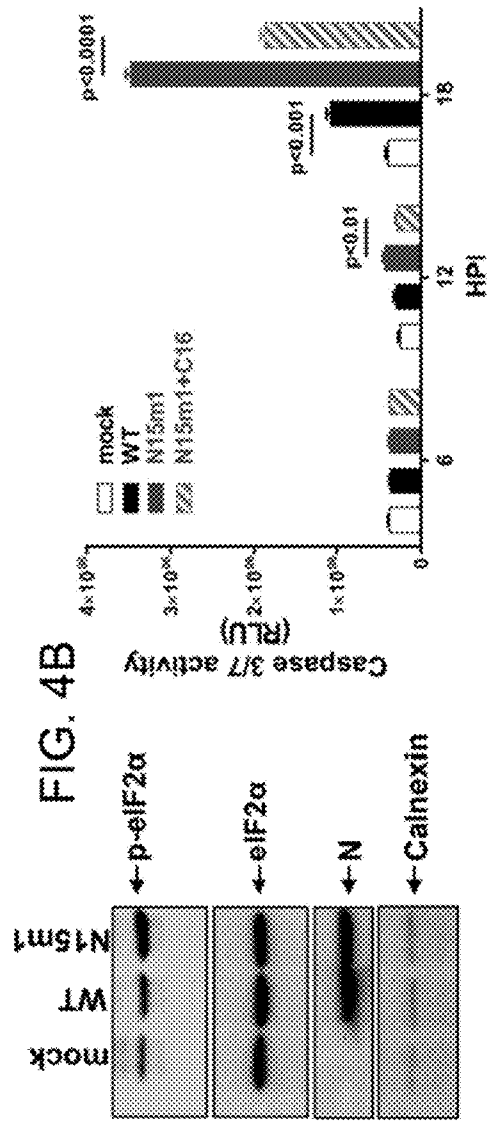
FIG. 4A
FIG. 4B
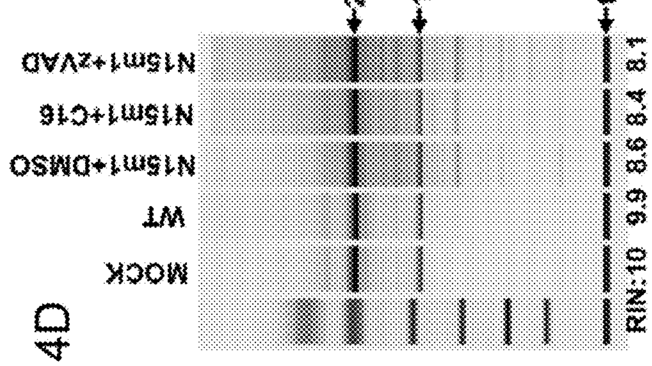
FIG. 4D
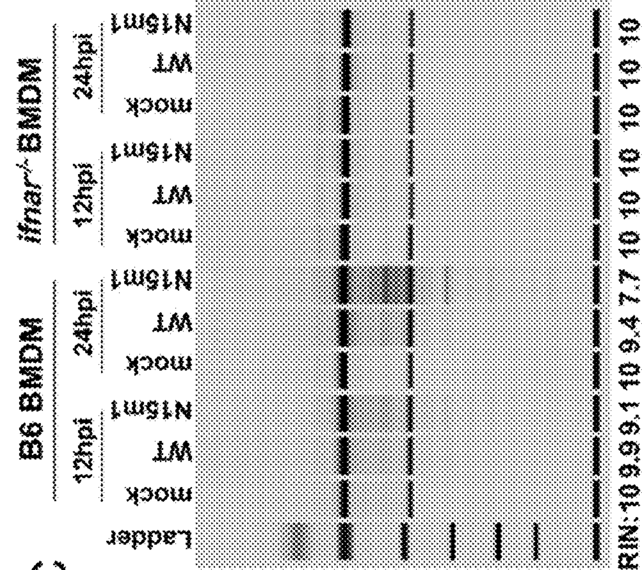
FIG. 4C

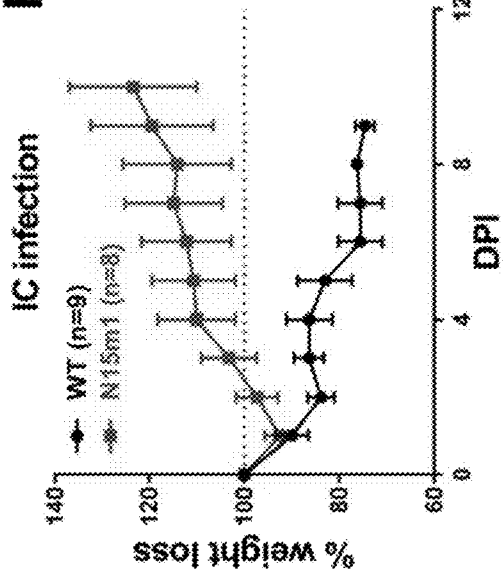
FIG. 8D
FIG. 8E
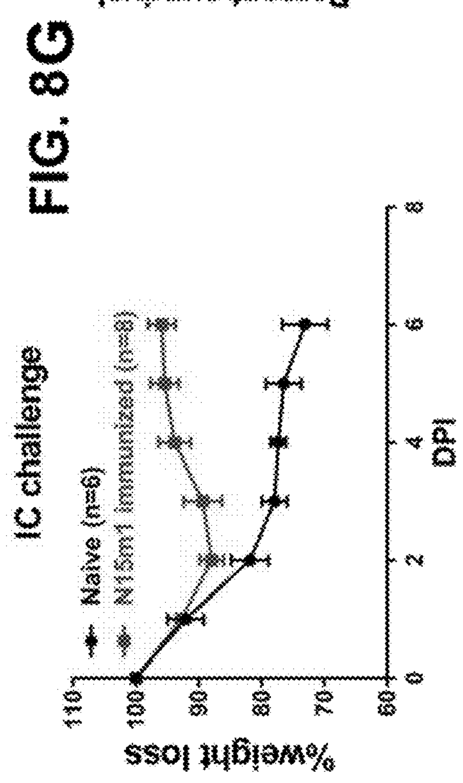
FIG. 8F
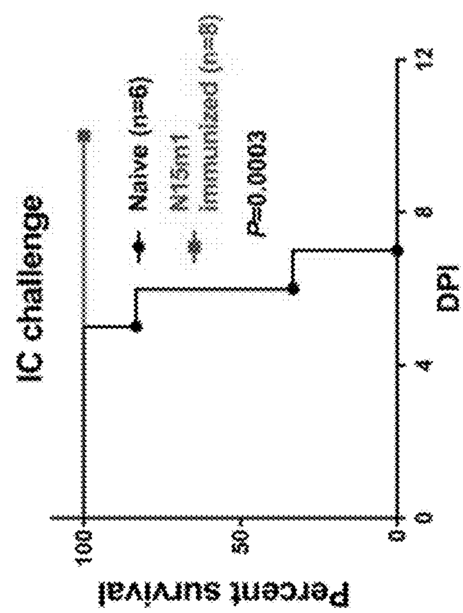
FIG. 8G

FIG. 9A 0 2 4 6 8 10 12 14 16 18 20 22 24 26 28 icPEDV

ORF1a ORF1b Spike 3 E M N icPEDV-deEndoU

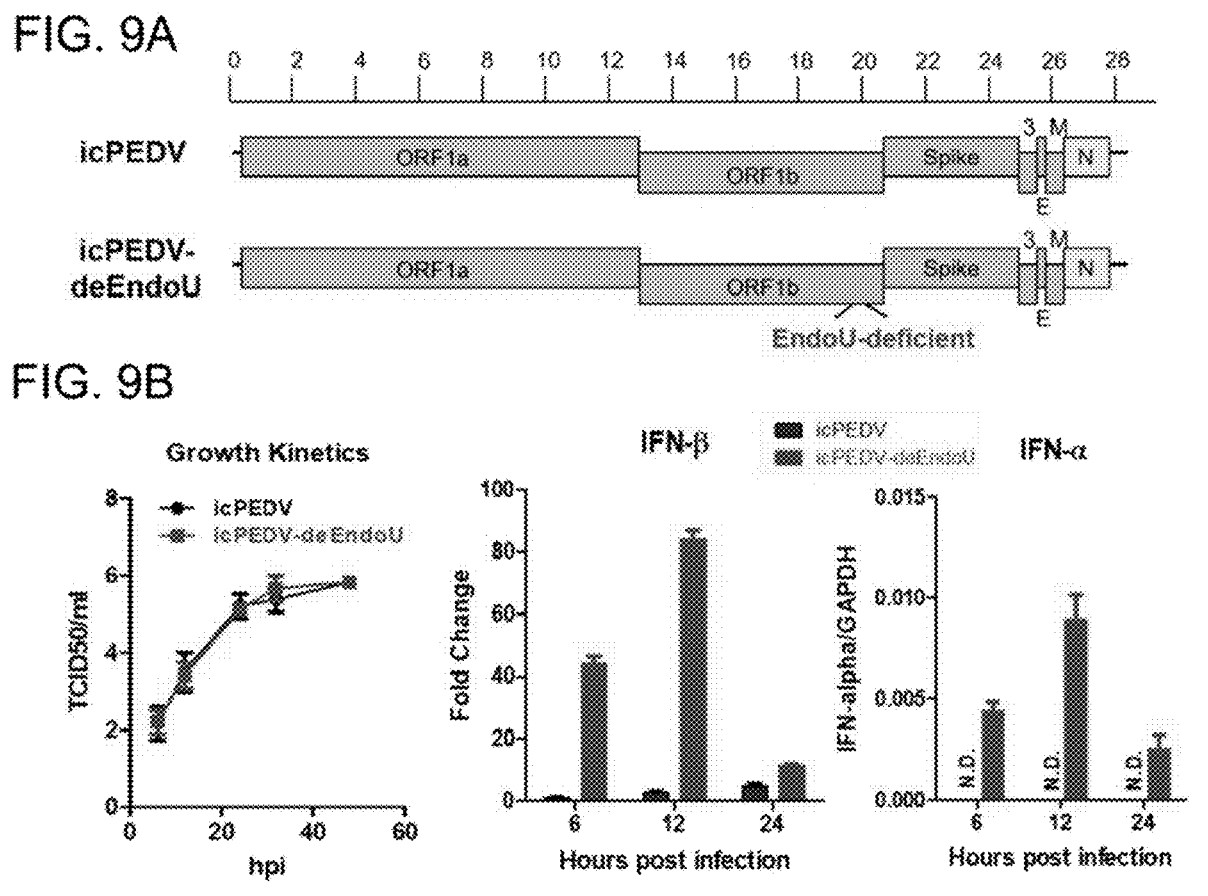

ORF1a ORF1b Spike 3 E M N

EndoU-deficient

FIG. 9B

Growth Kinetics

TCID50/ml icPEDV icPEDV-deEndoU hpi

IFN-β

Fold Change

Hours post infection

IFN-α

IFN-alpha/GAPDH

N.D

Hours post infection

CORONAVIRUSES, VACCINES COMPRISING THE SAME, AND METHODS FOR PREVENTING DISEASE

CROSS REFERENCE TO RELATED APPLICATIONS

This application claims the benefit of U.S. Provisional Application No. 62/466,779, filed Mar. 3, 2017 the contents of which are incorporated herein by reference.

STATEMENT REGARDING FEDERALLY SPONSORED RESEARCH

This invention was made with government support under Grant or Contract No. R01 A1085089 awarded by the National Institutes of Health, and Agricultural Research Service Project 5030-32000-118-11S awarded by the United States Department of Agriculture. The government has certain rights in the invention.

SEQUENCE LISTING

The instant application contains a Sequence Listing which has been submitted electronically in ASCII format and is hereby incorporated by reference in its entirety. Said ASCII copy, created on Jun. 6, 2018, is named B8-5129_SL.txt and is 43,750 bytes in size.

BACKGROUND OF THE INVENTION

The present invention generally relates to coronaviruses. The invention particularly relates to vaccines and methods of producing the same for existing and emerging coronaviruses.

Coronaviruses are species of viruses belonging to the subfamily Coronavirinae in the family Coronaviridae, and are positive-sense RNA viruses that infect humans and animals and cause respiratory, gastrointestinal or neurologic disease. Coronaviruses can emerge from animal reservoirs to cause significant epidemics in humans, exemplified by Severe Acute Respiratory Syndrome coronavirus (SARS-CoV) in 2002-2003 and Middle East Respiratory Syndrome coronavirus (MERS-CoV), which was recognized as an emerging virus in 2012. Remarkably, these viruses can replicate in the cytoplasm of macrophages, a cell type considered to be a critical innate sentinel for detecting and eliminating invading pathogens. Coronaviruses encode multiple interferon antagonists that likely function to impede and delay the activation of type I interferon (IFN) and interferon stimulated genes (ISGs) and that expression of a constellation of antagonists contributes to pathogenesis. A recent study using SARS-CoV infection of mice documented the delayed and limited production of interferon that contributes to disease.

Existing vaccine approaches for coronaviruses diseases are based on spontaneous natural attenuation, virus inactivation, and recombinant viral structural proteins via expression vectors. The existing vaccine candidates do not elicit robust protective immune responses. This lack of long term protection may be due to inefficient induction of innate immune response, such as type 1 interferons, which are critical molecules for promoting adaptive immunity and immune memory.

In view of the above, it can be appreciated that there is an ongoing desire to treat coronaviruses and that it would be desirable if a vaccine were available for inoculating subjects against various coronaviruses, including a vaccine that can stimulate both strong innate immune response and effective adaptive immune protection.

BRIEF DESCRIPTION OF THE INVENTION

The present invention provides mutant coronaviruses, vaccines comprising mutant coronaviruses, methods of producing vaccines, and methods of preventing disease in subjects.

According to one aspect of the invention, a live, attenuated coronavirus is provided that includes a variant replicase gene encoding polyproteins comprising a non-structural protein (nsp)-15. The replicase gene encodes the nsp15 and causes any change, including mutations and/or deletions, that affects the stability or activity of the nsp15.

Other aspects of the invention include variant replicase genes comprising the above-described coronavirus, proteins encoded by such variant replicase genes, plasmids comprising such variant replicase genes, vaccines comprising the above-noted coronavirus, and methods for treating or preventing a disease in a subject by administering such a vaccine to the subject.

According to another aspect of the invention, a method of preventing a disease in a subject is provided that includes activating type I interferon in the subject, wherein activation of the type I interferon reduces the pathogenicity of a coronavirus.

According to another aspect of the invention, a method of producing a vaccine is provided that includes modifying a wild-type coronavirus to produce a live, attenuated coronavirus comprising a variant replicase gene encoding polyproteins and causing a change, including mutations and/or deletions, in a non-structural protein (nsp)-15 that affects the stability or activity of the nsp15. A vaccine may be produced that includes the coronavirus and a carrier. Administering the vaccine to a subject causes activation of type I interferon in the subject which reduces the pathogenicity of the wild-type coronavirus.

Technical effects of coronavirus as described above preferably include the capability of inoculating a subject with a coronavirus that causes activation of type I interferon, which limits viral replication, dissemination, and disease.

Other aspects and advantages of this invention will be further appreciated from the following detailed description.

BRIEF DESCRIPTION OF THE DRAWINGS

FIGS. 1A through 1D include a schematic diagram of murine coronavirus genome highlighting nonstructural protein 15 and conserved residue threonine 98. FIG. 1A is a schematic diagram of the mouse hepatitis virus (MHV) A59 (MHV-A59) genome. PLP1/2: papain-like protease 1/2; ADRP, ADP-ribose-1'-monophosphatase; 3CL$^{pro}$, 3C-like protease; RDRP, RNA-dependent RNA polymerase; Hel, helicase; ExoN, 3'→5' exonuclease; NendoU, Nidovirus uridylate-specific endoribonuclease; 2'OMT, ribose-2'-O-methyltransferase. FIG. 1 B represents the crystal structure of nsp15, wherein the N domain, M domain, C domain are indicated at 90° C. rotation. T98 is shown in relation to L57 (N domain) and the catalytic residues (C domain). Protein Data Base ID: 2GTH. FIG. 1C indicates sites of mutation(s) for each coronavirus genotype and indication of induction of type I interferon in virus-infected bone marrow derived macrophages (BMDMs). FIG. 1C discloses SEQ ID NOS 1-6, respectively, in order of appearance. FIG. 1D indicates the sequence alignment of nsp15 T98 region from representative strains of coronavirus sub-groups using Clustal W. FIG. 1D discloses SEQ ID NOS 7-13, respectively, in order of appearance.

FIG. 2A indicates IFN-α11 mRNA levels in BMDMs infected with Wild-Type (WT) MHV or N15m1 by quantitative RT-PCR. Values were normalized to β-actin and analyzed using unpaired T test. FIG. 2B indicates secreted IFNα protein levels in supernatant of infected BMDMs detected by quantitative ELISA. Values were analyzed using 2way-Anova test. FIGS. 2C and 2D indicate growth kinetics of WT and N15m1 in B6 BMDMs and $ifnar^{-/-}$ BMDMs, respectively (MOI of 0.1). Viral titers of supernatants were collected at indicated hpi and titers were determined by plaque assay using 17Cl-1 cells. Values were analyzed using unpaired T test. Data are representative of 2-3 independent experiments and presented as Mean±SD.

FIG. 3A indicates BMDMs were infected with WT, N15m1, or UV-inactivated N15m1 (UV-N15m1) MHV. At 24 hpi, cell viability of viral infected-BMDMs were quantified using CellTiter Glo assay. Values were analyzed using unpaired T test. FIG. 3B indicates BMDMs were infected with WT, or N15m1 MHV and subsequently treated with either DMSO, zVAD (20 μM), Necrostatin-1 (Nec-1) (25 μM), or VX-765 (20 μM). Cell viability was measured at 24 hpi by CellTiter Glo assay. Values were analyzed using unpaired T test. FIG. 3C indicates BMDMs were inoculated with WT or N15m1 MHV and zVAD (20 μM) was added to the media. At 24 hpi, caspase 3/7 activity was determined by a caspase 3/7-Glo activity assay. Values were displayed in relative light units (RLU) and analyzed using 2way-Anova test. FIG. 3D indicates BMDMs were infected with WT or N15m1 MHV and cell lysates were collected at indicated time points. Western blot detection of cleaved-caspase 3 and N protein. All infections are at an MOI of 0.1. Data are representative of 2-3 independent experiments and presented as Mean±SD.

FIGS. 4A through 4D indicate MHV nsp15 mutant virus infection activates host dsRNA sensors. FIG. 4A indicates BMDMs were infected with WT or N15m1 MHV (MOI of 0.1). At 16 hpi, cells were lysed and 40 μg cell lysate was detected for phospho-eIF2α, eIF2a and viral N protein by western blot. Calnexin serves as a loading control. FIG. 4B indicates PKR inhibitor blocks N15m1-induced apoptosis in B6 BMDMs. Cells were infected with WT or N15m1 (MOI of 0.1) and subsequently treated with the PKR inhibitor C16 (1 μM). Cells were collected and evaluated for caspase 3/7 activity at indicated time points. Values were displayed in relative light units (RLU) and analyzed using 2way-Anova test. FIG. 4C indicates an RNA degradation pattern of 300 ng total RNA extracted from infected-BMDMs using a bioanalyzer (MOI of 1). The RNA integrity numbers (RIN) and the positions of 28S, 18S rRNAs, and tRNA are shown to the bottom and the right of image, respectively. FIG. 4D indicates an RNA degradation pattern of RNAs from infected-BMDMs (MOI of 0.1) treated with C16 inhibitor (1 μM) or zVAD (20 μM) at 18 hpi. Data are representative of 2-3 independent experiments.

FIG. 5A indicates BMDMs infected with WT or N15m1 virus at an MOI of 0.1 were lysed at 16 hpi, and viral N protein, nsp15, and β-actin were detected by western blotting. FIG. 5B indicates WT and T98M mutant of nsp15 were expressed and purified from *E. coli*. Coomassie blue staining shown the purified Sumo-tagged nsp15 and T98M, which were detected by nsp15 antibody using western blotting (bottom). FIG. 5C indicates Differential Scanning Fluorimetry (DSF) thermal shift analysis of nsp15 wild type (black) and nsp15-T98M mutant (red) protein. FIG. 5D indicates a radiolabeled RNA molecule R16.4 was treated over time with WT Nsp15 or T98M in the presence of 5 mM Mn2+. At the indicated time-point, an aliquot of the reaction was analyzed on a denaturing 20% polyacrylamide gel. The sequence of RNA R16.4 is shown above the gel image. The only uridylate, at position 13, is underlined. Data are representative of 2-3 independent experiments. FIG. 5D discloses SEQ ID NO: 14.

FIG. 6A indicates B6 BMDMs were infected with WT or nsp15 mutant viruses (N15m1 or N15m3) at an MOI of 0.1. At 12 hpi, total RNA was extracted and analyzed for IFN-α11 mRNA levels. Values were presented as Mean±SD and analyzed using unpaired T test. FIG. 6B indicates B6 or $ifnar^{-/-}$ BMDMs were infected WT or N15m3 at an MOI of 0.1. At indicated time points, cell supernatants were collected for plaque assay in 17CL-1 cells. Values were presented as Mean±SD and analyzed using unpaired T test. FIG. 6C indicates B6 BMDMs were infected with WT or N15m3 at an MOI of 0.1 and harvested for analysis of caspase 3/7 activity at indicated time points. Values were presented as Mean±SD and analyzed using unpaired T test. FIG. 6D indicates RNA degradation pattern of 500 ng total RNA extracted from infected-BMDMs using a bioanalyzer (MOI of 0.1). The RNA integrity numbers (RIN) and the positions of 28S, and 18S rRNAs are pointed to the bottom and the right of image, respectively. Data are representative of 2-3 independent experiments.

In FIGS. 7A and 7B, BMDMs were infected with WT or N15m3 at MOI of 0.1. Cells were fixed at 6 hpi and stained with anti-dsRNA, anti-nsp2/3, and Hoescht 33342 (FIG. 7A) or anti-dsRNA, anti-nsp15, and Hoescht 33342 (FIG. 7B). Surfaces for puncta were created based on dsRNA fluorescence, and nsp fluorescence was measured within each surface. The number of foci from 25 images was counted using IMARIS software program. Ratio of dsRNA/nsp2/3 was calculated by dividing total dsRNA foci by the number of nsp2/3 foci (FIG. 7A). Percent co-localization of nsp15 with dsRNA was calculated by dividing dsRNA+nsp15+ foci by total dsRNA foci. Values were analyzed by unpaired T test. Scale bar: 5 μM.

FIGS. 8A through 8G indicate MHV Nsp15 mutant virus is highly attenuated in mice and induces a protective immune response. FIG. 8A indicates Virus burden in organs from mice infected with WT or N15m1 virus. Six-week old C57BL/6J mice (n=4) were intraperitoneally inoculated with 6.0×104 PFU virus. Liver and spleen were harvested at indicated time points and tested for viral titer by plaque assay. Red dash line is an indication of limit of detection. FIG. 8B indicates C57BL/6J mice were intraperitoneally inoculated with 6.0×104 PFU virus. At 24 hpi, mesenteric lymph nodes (MLN) were harvested and viral genomes were measured by quantitative RT-PCR targeting N gene. Values are normalized to β-actin. *, p<0.001, unpaired t test. FIG. 8C indicates liver pathology by Hematoxylin and Eosin (H&E) staining as indicated by arrows in WT and N15m1-infected mice. Data are representative of 5 mice. In FIGS. 8D and 8E, mice were inoculated by intracranial (IC) injection with 600 PFU of WT or N15m1 virus. Viral pathogenicity was measured by percent body weight loss (FIG. 8D) and percent survival (FIG. 8E). In FIGS. 8F and 8G, thirteen-week old naïve mice and N15m1-infected mice from FIG. 8D were challenged with 6.0×103 PFU WT virus by intracranial (IC) inoculation. Viral pathogenicity was measured by percent body weight loss (FIG. 8F) and percent survival (FIG. 8**G). Mouse numbers (n) are indicated. The p values of survival rate were calculated using log-rank test.

FIGS. 9A and 9B indicate porcine epidemic diarrhea virus (PEDV) EndoU-deficient mutant augments type I interferon production in infected-porcine macrophages. FIG. 9A is a schematic diagram of infectious clones of wild-type PEDV (icPEDV) and a PEDV nsp15 mutant virus (icPEDV-deEndoU). FIG. 9B indicates Vero cells were infected with 0.1 plaque forming unit/cell of either icPEDV or icPEDV-deEndoU. At indicated time points, cell supernatants were collected for viral titration. The data demonstrate that both icPEDV and icPEDV-deEndoU propagated efficiently in Vero cells and exhibited a similar growth kinetics. FIG. 9C indicates primary porcine alveolar macrophages (PAMs) were infected with either icPEDV or icPEDV-deEndoU virus and harvested at indicated time points. Total RNA was extracted from the harvested cells and was transcribed into cDNA. The production of type I interferons (IFN-α and IFN-β) was evaluated by examining their mRNA levels using quantitative PCR. The data demonstrates that the PEDV deEndoU mutant virus stimulates a significant high level of type I IFN production in PAMs compared to wild-type PEDV infection (N.D.=not detected).

FIG. 10A indicates BMDMs were infected with WT or N15m1 MHV (MOI of 0.1). At 12 hpi, infected cells were fixed with 4% formaldehyde and stained with Hoechst 33342 (nucleus; blue), anti-nucleocapsid (N; red), and anti-ISG54 (green). Immunofluorescence was detected by confocal microscopy. FIG. 10B indicates BMDMs were infected with WT, N3m, or N15m1 MHV (MOI of 0.1). IFN-α11 mRNA levels were determined at 12 hpi by quantitative RT-PCR. Values normalized to β-actin. n.s., not significant, unpaired t test.

FIG. 11A indicates B6 BMDMs were infected with WT, N15m1, or UV-inactivated N15m1 (UV-N15m1) MHV. At 24 hpi, cytopathic effect was observed under bright-field microscopy. FIG. 11B indicates condensation of nuclear chromatin (black arrows) indicative of apoptosis was determined by electron microscopy in BMDMs treated with staurosporine (1 μM) or infected with WT or N15m1 MHV at 16 hpi.

FIG. 12A indicates B6 BMDMs were infected with WT or N15m1 at an MOI of 0.1. Cytopathic effect and cell viability were evaluated at 18 hpi. **, p<0.0001, unpaired T test. FIG. 12B indicates B6 or ifnar$^{-/-}$ BMDMs were infected with WT or N15m1 at an MOI of Caspase 3/7 activity was measured at 18 hpi by a Caspase 3/7-Glo assay. , p<0.0001, 2way-Anova test. Data are representative of 2-3 independent experiments. Data in FIG. 12**B are displayed in relative light units (RLU) and presented as Mean±SD.

FIG. 14A indicates at 24 hpi, cell viability was determined using CellTiter Glo assay. Values were analyzed by unpaired T test. FIG. 14B indicates at 12 hpi, cell was harvested and 20 μg total lysate was used for the detection of nsp15, N protein, and loading control (β-actin).

FIG. 16A indicates the number of dsRNA and nsp2/3 foci were counted in ifnar$^{-/-}$ BMDMs. FIG. 16B indicates the localization of dsRNA and nsp2/3 in B6 BMDMs. The number of dsRNA and nsp2/3 foci were counted and the ratio of dsRNA/nsp2/3 was calculated by dividing total dsRNA foci by the number of nsp2/3 foci (FIG. 16A). Values were analyzed by unpaired T test. Scale bar: 5 μM.

DETAILED DESCRIPTION OF THE INVENTION

Figure 2A:
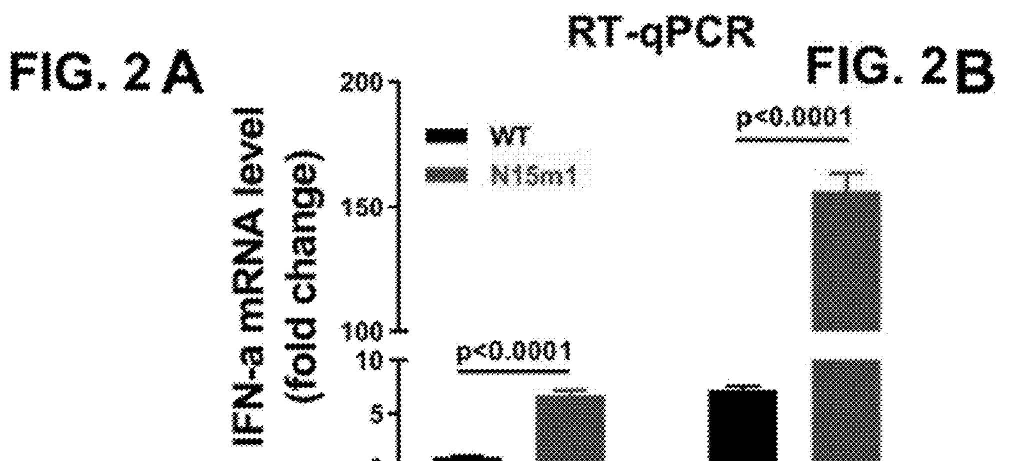
FIGS. 2A through 2D indicate that MHV nsp15 mutant virus activates expression of type I interferon and is impaired for replication in BMDMs.

The present disclosure provides mutant coronaviruses, vaccines comprising mutant coronaviruses, methods of producing vaccines, and methods of preventing disease.

RNA viruses that replicate via dsRNA intermediates can be detected as "non-self" by host dsRNA sensors, including cytoplasmic RIG-like receptors (RLRs). Activation of RLRs stimulate the production of interferon, which upregulates additional dsRNA sensors, such as PKR and the OAS/RNase L system, and hundreds of antiviral interferon-stimulated genes (ISGs). Additionally, interferon secreted from virus-infected cells that successfully sense the dsRNA can induce an antiviral state in neighboring cells and limit replication of potentially invading RNA viruses. Thus, many viruses have evolved strategies to sequester dsRNA to escape detection by host sensors. This disclosure presents a previously unrecognized role for coronavirus nsp15 in blocking the activation of dsRNA sensors in macrophages, thus enabling viral replication and the dissemination of the progeny virus.

To investigate coronavirus antagonism of the interferon response, investigations leading to the present invention tested mouse hepatitis virus strain A59 (MHV-A59), a model coronavirus that replicates in multiple murine cell types, including macrophages, and can cause acute hepatitis or lethal encephalitis, depending on the site of injection. The viral genomic RNA is thirty-two kilobases and two-third of the genome encodes a large replicase polyprotein, while the remainder of the genome codes for structural proteins and strain-specific accessory proteins (FIG. 1A). The replicase polyprotein is processed by viral proteases into sixteen nonstructural proteins (nsp's). The viral nsp's assemble together with host endoplasmic reticulum to generate convoluted membranes and double membrane vesicles (DMVs), which are the sites of viral RNA synthesis. Coronavirus RNA replication proceeds via the generation of a nested-set of negative-strand RNAs that serve as the templates for synthesis of new positive-strand genomes and mRNAs. Double-stranded RNA (dsRNA) intermediates, potent stimulators of cytoplasmic innate sensors, are produced during this process and visualized in association with the DMVs. A potential function for coronavirus DMVs may be to sequester viral dsRNA away from host dsRNA sensors. However, it is unclear if DMVs alone are sufficient to prevent activation of the host innate immune response. Investigations reported herein surprisingly showed that coronavirus nonstructural protein 15 (nsp15), a highly conserved Nidovirus (coronaviruses and arterivuses) component with endoribonuclease activity, acts in conjunction with the viral replication complex to limit the exposure of viral dsRNA to host dsRNA sensors.

Nsp15 is a nonstructural protein generated by viral protease-mediated processing of the replicase polyprotein (FIG. 1A). Bioinformatic analysis revealed that the nsp15 contains a domain with distant homology to cellular endoribonucleases, termed NendoU, which is highly conserved in vertebrate Nidoviruses. Structural and biochemical studies revealed that SARS-CoV and MHV nsp15, and the arterivirus ortholog nsp11 can assemble to form oligomers and cleave ssRNA and dsRNA molecules with a 3' uridinylate preference. However, the role of endoribonuclease activity in Nidovirus replication and pathogenesis has previously not been well understood. Researchers were unable to recover human CoV 229E virus encoding an endoribonuclease catalytic site mutant, and therefore concluded that nsp15 was essential for coronavirus replication; while MHV encoding nsp15 catalytic site mutations replicated to reduced titers (about one log) in fibroblast cell lines.

Investigations leading to the present invention determined that nsp15 is not required for viral RNA synthesis per se, but acts to mediate evasion of host dsRNA sensors. Specifically, coronaviruses encoding mutations in nsp15, which either renders nsp15 unstable or disables endoribonuclease activity, activate interferon and dsRNA sensors PKR and OAS to promote apoptotic cell death in macrophages. Therefore, nsp15 is essential for virus infection and dissemination in mice, and that a nsp15 mutant virus can induce a protective immune response.

Nonlimiting embodiments of the invention will now be described in reference to experimental investigations leading up to the invention.

Figure 2B:
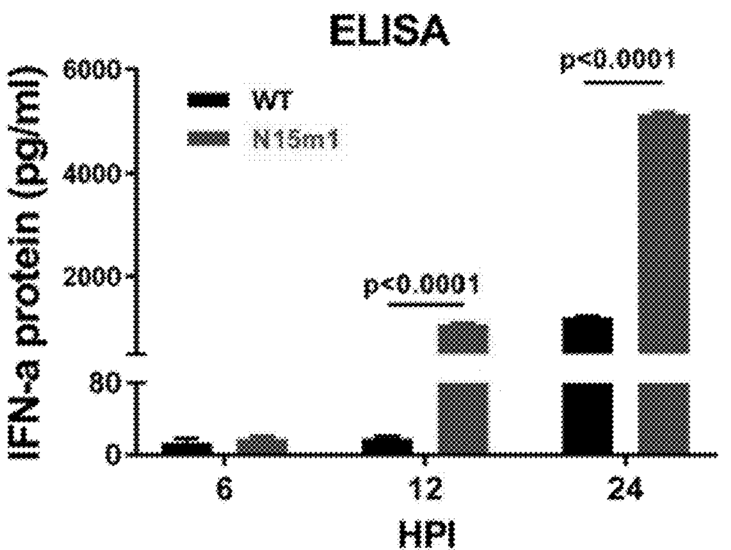
Figure 10A:
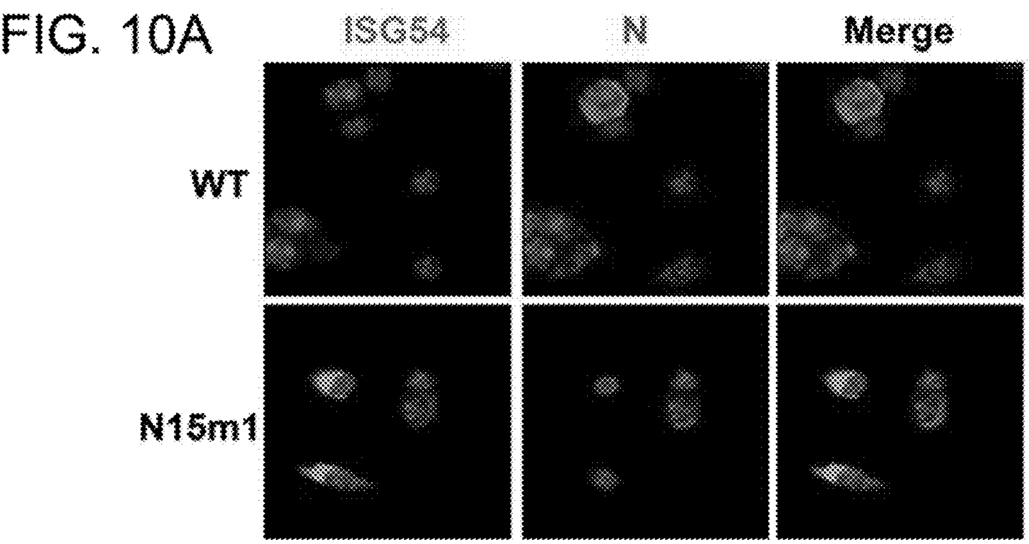
FIGS. 10A and 10B indicate N15m1, but not N3m virus, induces IFN activation.
Figure 10B:
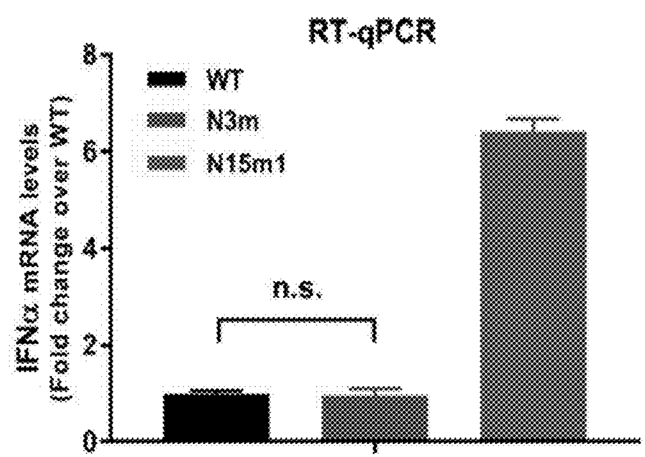

Screening methods were used to identify mechanisms used by coronaviruses to block the innate immune response, particularly the activation of type I interferon (IFN-$\alpha$/$\beta$). These screenings identified a viral isolate, designated N15m1, which elicited production of IFN-$\alpha$ upon infection of murine bone marrow-derived macrophages (BMDMs) (summarized in FIG. 1C). Deep sequencing of viral genomic RNA revealed that N15m1 contains a mutation in nsp15 (threonine 98 to methionine [T98M]) and a mutation in nsp3 (arginine 971 to alanine [R971A]). Infection of macrophages with N15m1 activated the transcription of IFN-$\alpha$ as detected by quantitative PCR (qPCR) (FIG. 2A), and increased the amount of secreted IFN-$\alpha$ protein, as detected by ELISA (FIG. 2B). A consequence of type I interferon activation was upregulation of the interferon-stimulated ISG54, as detected by immunofluorescence staining (FIG. 10A). The threonine-98 residue in nsp15 is highly conserved in coronaviruses (FIG. 1D) and may be critical for functionality. In addition, a "clean" nsp3 mutant virus, designated N3m (FIG. 1C), was engineered which harbors only the R971A mutation. N3m retained the ability to antagonize interferon as WT virus (FIG. 10B), further suggesting that the T98M mutation in nsp15 is responsible for the loss of IFN-$\alpha$ antagonism.

Figure 2C:
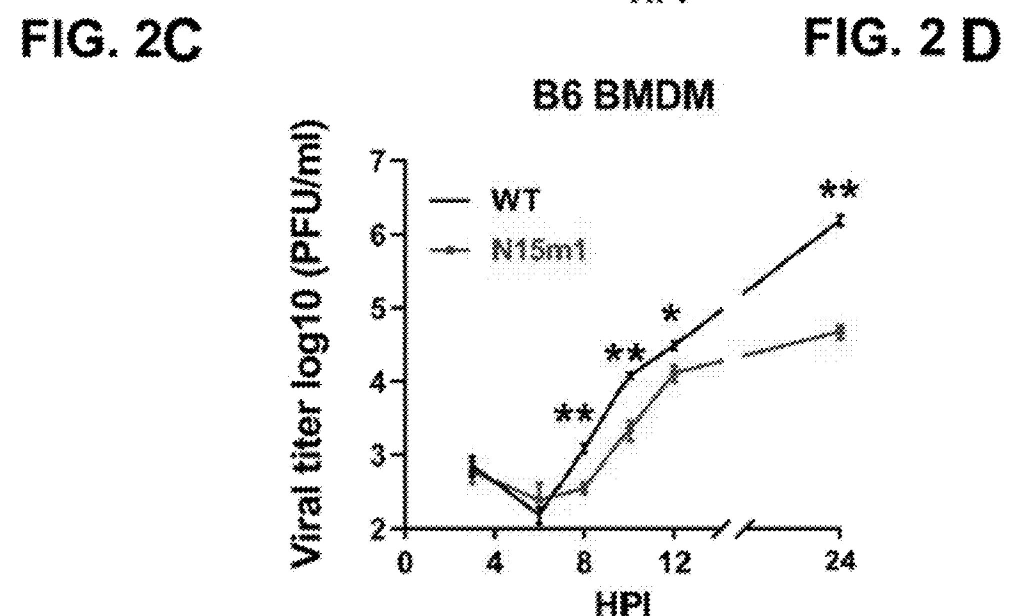

To determine whether the expression of IFN-$\alpha$ and ISGs altered virus replication kinetics or titer, wild-type (B6) and type I interferon receptor-deficient (ifnar$^{-/-}$) BMDMs were infected with either WT or N15m1 virus at a low multiplicity of infection (MOI of 0.1), and monitored virus production over time. The replication of N15m1 was significantly delayed and reduced in B6 BMDMs and the level of progeny virus produced was significantly lower than that of WT virus after 8 hpi (FIG. 2C). This replication deficiency of N15m1 was not observed in ifnar$^{-/-}$ BMDMs as N15m1 had similar kinetics as WT virus (FIG. 2D), consistent with the idea that interferon limits virus replication. Taken together, it was concluded that the T98M mutation in nsp15 results in a virus that fails to block the activation of type I interferon in macrophages. These results indicate that the wild-type nsp15 functions as a type I IFN antagonist in the context of viral infection.

Figure 3A:
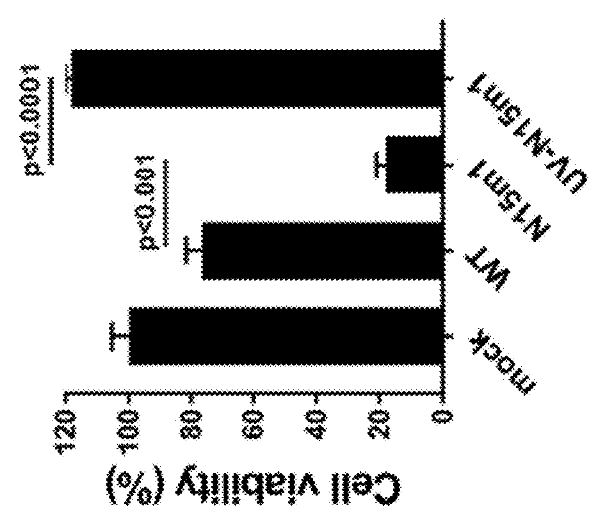
FIGS. 3A through 3D indicate MHV nsp15 mutant virus induces a rapid apoptotic cell death in BMDMs.
Figure 3B:
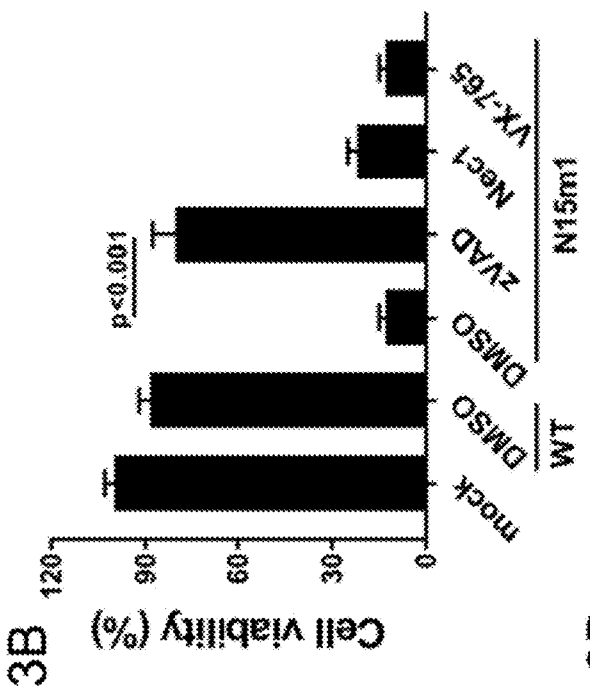
Figure 3C:
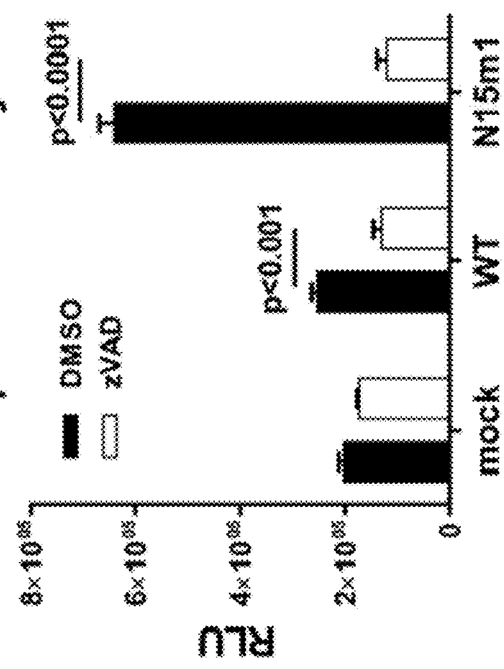
Figure 3D:
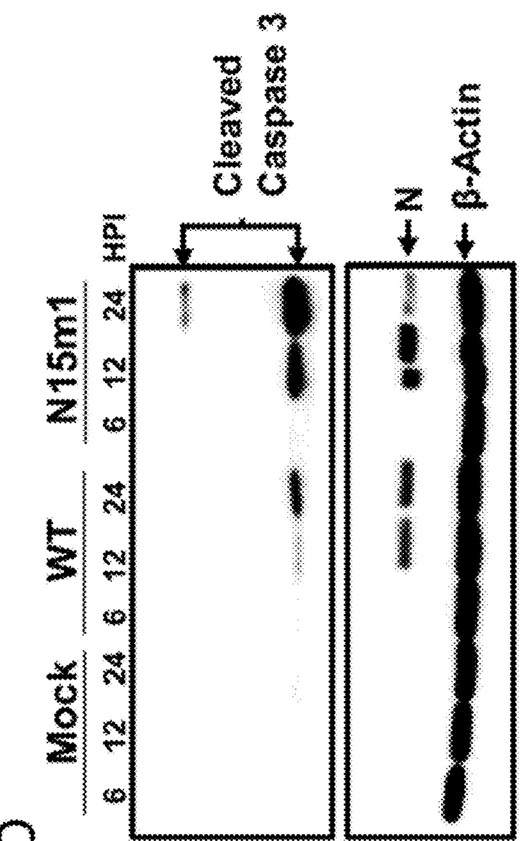
Figure 11A:
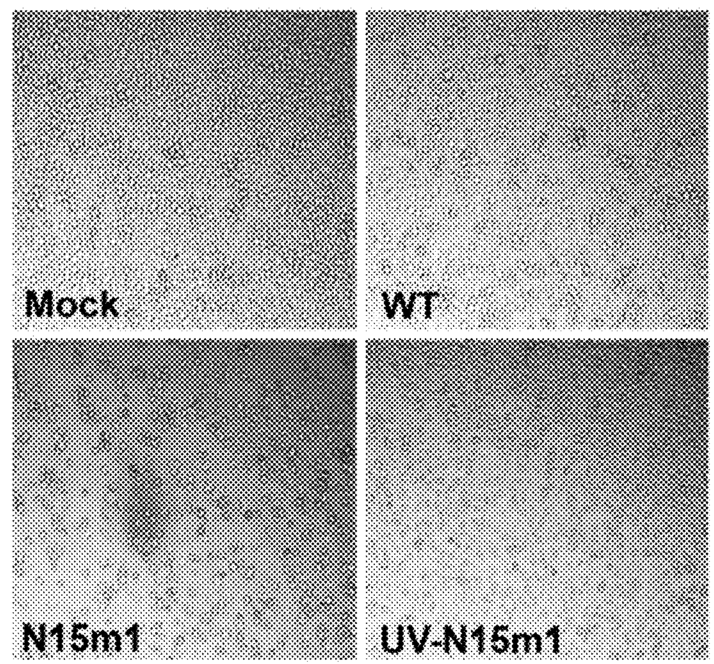
FIGS. 11A and 11B indicate N15m1 induces a rapid apoptotic cell death.
Figure 11B:
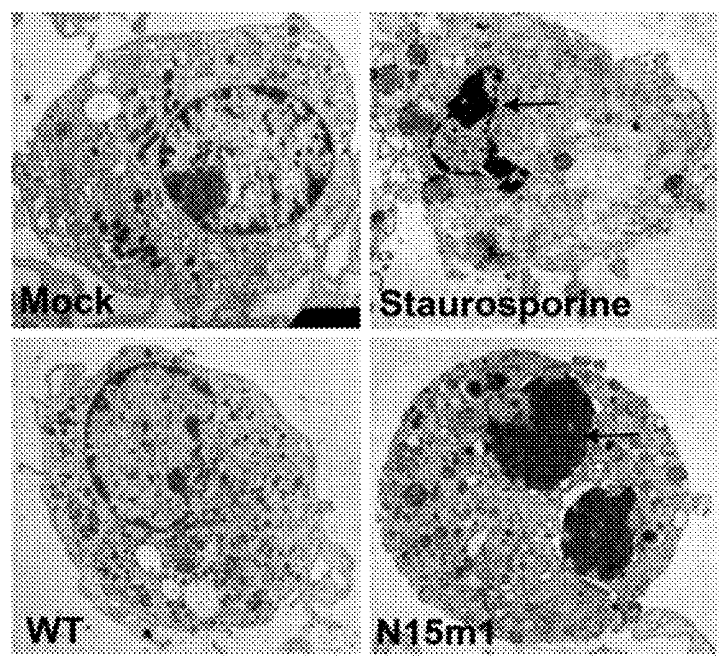

While performing the growth kinetic experiments described above, it was observed that N15m1-infected macrophages died more rapidly than cells infected with either WT virus or UV-inactivated virus. As shown in FIG. 3A, N15m1-infected BMDMs had a significantly lower cell viability at 24 hpi (see also FIG. 11A). In addition, the pan-caspase inhibitor zVAD, but not the RIPK1 inhibitor Nec-1 or caspase-1 inhibitor VX-765, prevented virus-induced cell death (FIG. 3B). These results indicated that N15m1 infection activates apoptotic cell death rather than RIPK1/RIPK3-dependent necroptosis or caspase-1-mediated pyroptosis. This finding was supported by assessing other hallmarks of apoptosis: enhanced caspase-3/7 activity in N15m1-infected BMDMs that is inhibited by zVAD (FIG. 3C); activation of the caspase3/7-dependent apoptosis pathway was also demonstrated through detection of increased levels of cleaved caspase-3 products (FIG. 3D); and condensed, marginalized chromatin, and nuclear fragmentation were observed by electron microcopy (EM) in N15m1—compared to WT-infected BMDMs (FIG. 11B). Taken together, these data demonstrated that N15m1 infection induces apoptosis in macrophages, suggesting that WT nsp15 not only antagonizes activation of type I interferon, but also prevents apoptotic cell death.

Figure 12A:
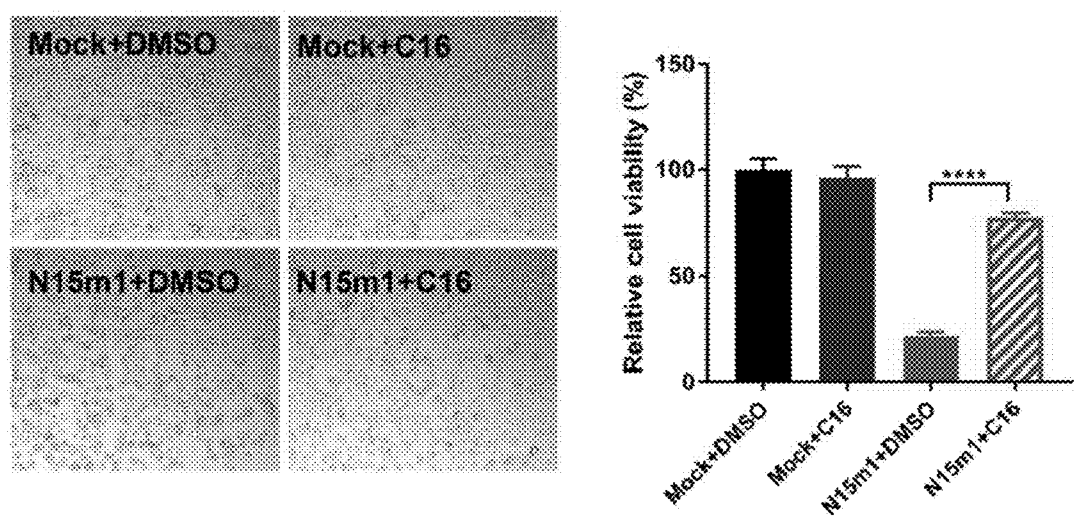
FIGS. 12A and 12B indicate N15m1-induced apoptosis can be inhibited by PKR inhibitor C16 and requires type I IFN receptors.

Type I interferon synthesis and apoptotic cell death are triggered by host membrane-associated or cytoplasmic sensors that recognize viral dsRNA. The dsRNA-dependent activation of interferon-stimulated genes 2'5'-oligoadenylate synthetase (OAS) and protein kinase R (PKR) can trigger apoptotic cell death. Previous studies have shown that SARS-CoV and MHV nsp15 is a viral endoribonuclease and can both bind to and cleave RNA molecules (ssRNA and dsRNA). Therefore, it was hypothesized that WT nsp15 may block interferon synthesis and prevent apoptosis by sequestering dsRNA from host sensors. To address whether nsp15 prevents the activation of dsRNA sensors, the levels of phosphorylated eIF2$\alpha$, an indicator of PKR activation, and degradation of ribosomal RNA (rRNA), an indicator of active 2'5'-OAS/RNaseL system signaling were evaluated. Increased phosphorylation of eIF2$\alpha$ was observed in BMDMs infected with N15m1 when compared to infection by WT virus (FIG. 4A). Addition of the specific PKR kinase inhibitor C16 significantly reduced the levels of caspase 3/7 activation that is associated with apoptosis in N15m1-infected cells (FIGS. 4B and 12A).

Figure 12B:
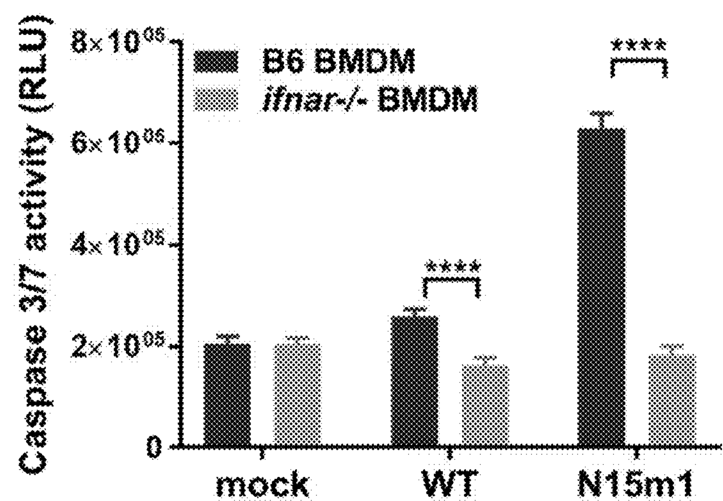

The activation of the 2'5'-OAS/RNaseL pathway was also observed, as revealed by degradation of rRNA at 12 and 24 hpi (FIG. 4C). Degradation of host rRNA was not inhibited by zVAD or C16 (FIG. 4D), indicating that activation of 2'5'-OAS/RNaseL was not a consequence of apoptosis, and was independent of the PKR pathway. Finally, caspase-3 cleavage or activation of caspase-3/7 in N15m1-infected macrophages were dependent on the IFN receptor (FIGS. 4C and 12B), further suggesting that the observed apoptosis depends on interferon-stimulated genes. Taken together, these data suggested that during N15m1 infection of macrophages, viral dsRNA detection triggers eIF2α phosphorylation, RNA degradation, activation of caspase 3/7, and apoptosis. These results supported the hypothesis that WT nsp15 functions to prevent dsRNA-mediated activation of innate immune responses.

Figure 2D:
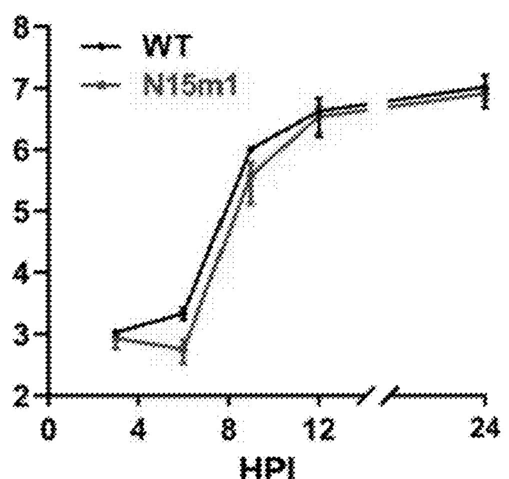
Figure 5A:
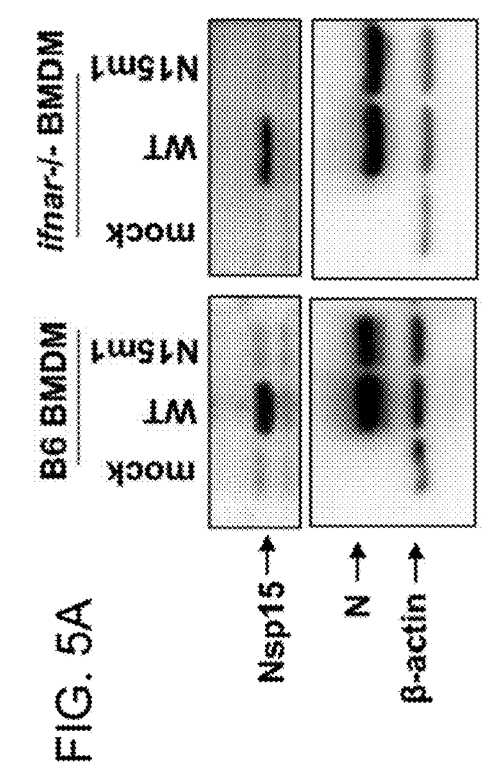
FIGS. 5A through 5D indicate T98M mutation causes nsp15 protein instability.
Figure 5B:
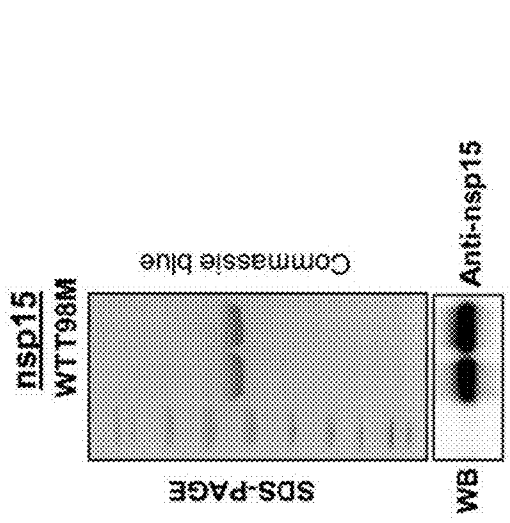

The T98M mutation resides at the interface between the N-terminal domain and middle domain of nsp15 (FIG. 1B), which could affect stability or assembly of oligomers. Indeed, it was found that the level of nsp15 was significantly reduced in N15m1-infected cells when compared to WT-infected cells, while the level of N protein was only minimally reduced (FIG. 5A). The decreased level of nsp15 in N15m1-infected B6 BMDMs was not solely due to the reduction of viral replication because the reduction was also observed in N15m1-infected ifnar$^{-/-}$ BMDMs (FIG. 5A), where both viruses had similar levels of N protein and similar growth kinetics (FIG. 2D). The reduced detection is also not due to the affinity of nsp15 antibodies to mutated protein as both wild-type and T98M nsp15 proteins purified from *E. coli* were detected equivalently by nsp15 polyclonal antisera (FIG. 5B, bottom). These results suggested that the T98M mutation destabilizes nsp15, resulting in a decrease in the steady-state level of the protein in N15m1-infected cells.

Figure 5C:
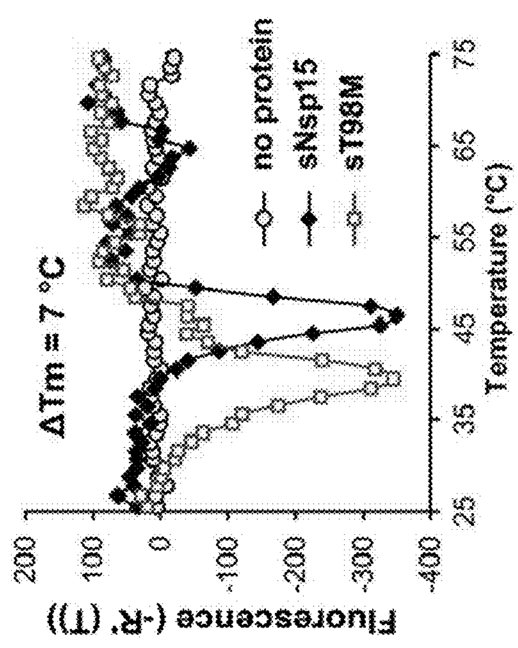

To further evaluate the effect of the T98M mutation on the nsp15 protein, codon-optimized versions of the wild-type and T98M nsp15 proteins were cloned and expressed as SUMO-fusion proteins in *E. coli* (FIG. 3B, top). Based on the structure of the nsp15, the SUMO tag will not affect the assembly of oligomers, such as hexamers previously reported for nsp15. To further evaluate if the T98M mutation destabilizes the protein, differential scanning fluorimetry (DSF) was used to measure the stability of the nsp15 in response to heat (FIG. 5C). WT nsp15 exhibits a major transition to the denatured state at 47° C. In contrast, the T98M mutant denatured at 40° C., seven degrees lower than the WT nsp15, further indicating that the T98M mutation renders nsp15 less stable.

Figure 5D:
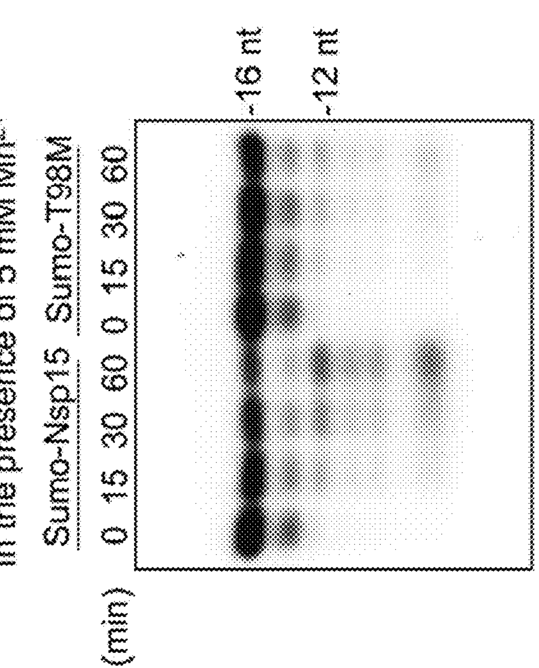
Figure 13:
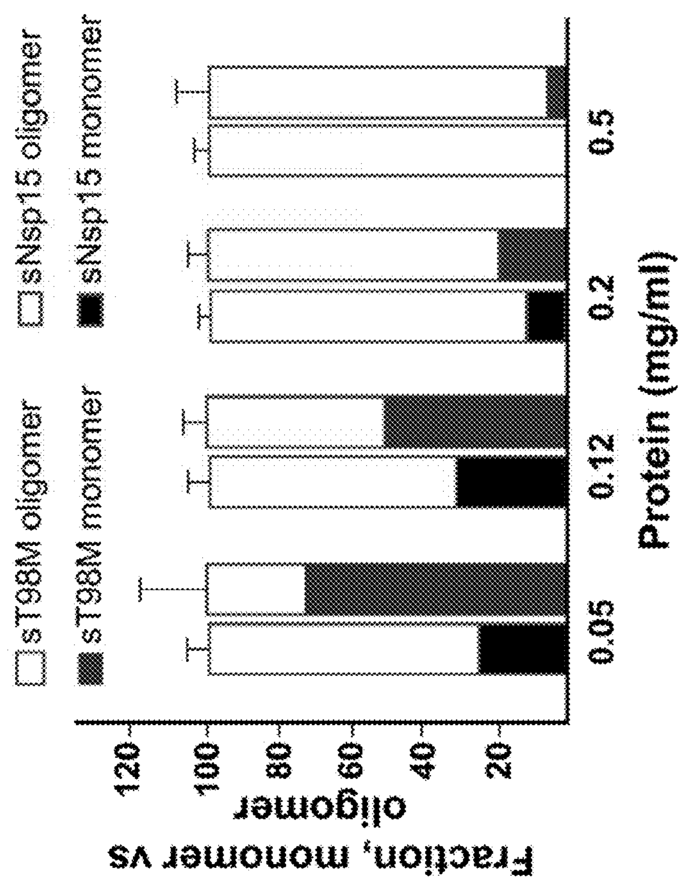
FIG. 13 indicates T98M mutation alters the oligomerization of nsp15. Dynamic Light Scattering was used to evaluate the percent monomer and hexamer present at increasing concentrations of WT and T98M nsp15.

Using dynamic light scatter (DLS) spectrometry, it was found that the majority of WT nsp15 assembles to form oligomers at a protein concentration of 0.05 mg/ml (FIG. 13). In contrast, the major of the nsp15-T98M mutant was detected in the monomeric form under these conditions (FIG. 13). To determine if impaired or lack of oligomerization of nsp15-T98M affected endoribonuclease activity, an evaluation was conducted that found that the T98M mutant exhibited a significant reduction in RNA cleavage activity compared to WT protein (FIG. 5D). Together, the in vitro characterizations of the WT and T98M nsp15 proteins demonstrated that T98M mutation decreases protein stability and impairs endoribonuclease activity. These results were interpreted to further demonstrate that a variant replicase gene encoding polyproteins comprising nsp15 and causing any change, including mutation(s) and/or deletion(s), in nsp15 has the ability to affect the stability (destabilize) or activity (inactivate) of nsp15.

Figure 6A:
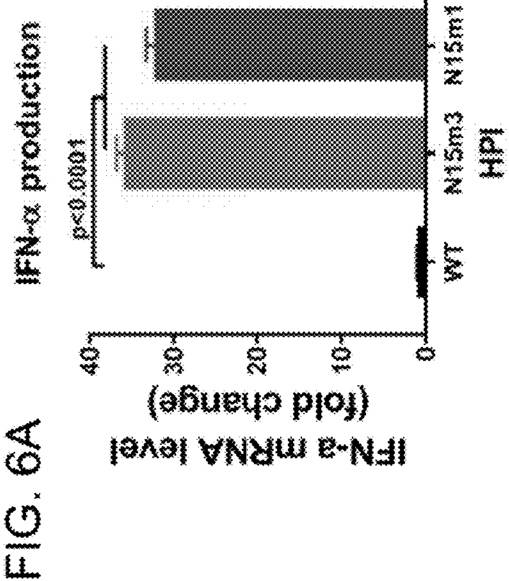
FIGS. 6A through 6D indicate N15m3 virus (nsp15-H262A) phenocopies N15m1 virus in the loss of interferon antagonism.
Figure 14A:
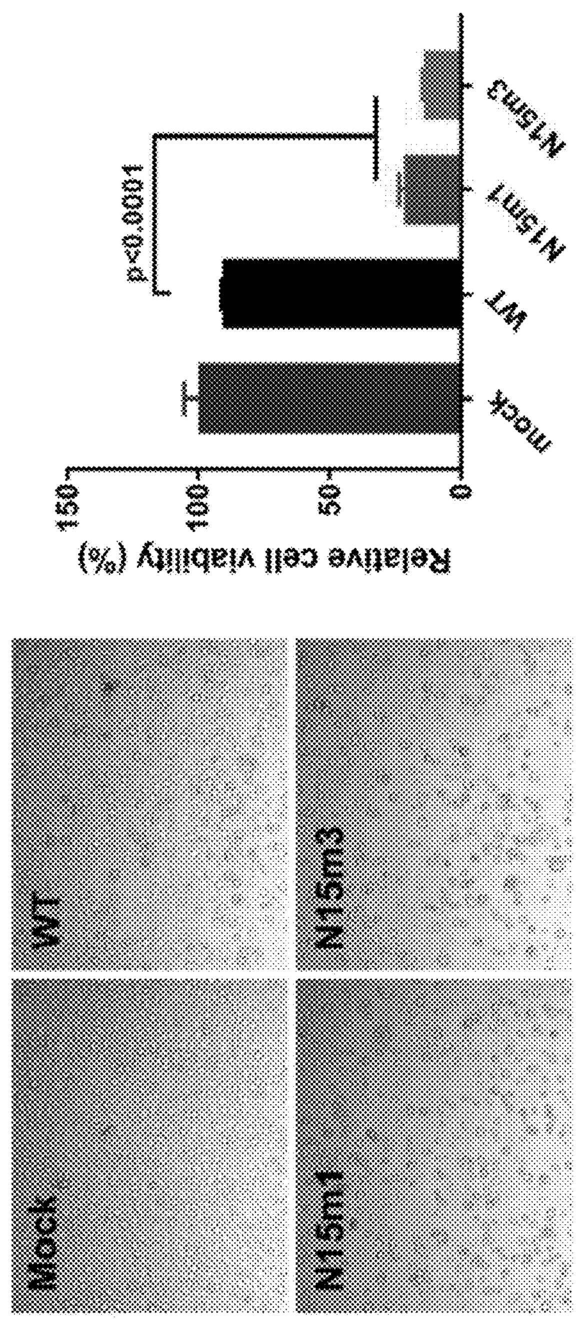
FIGS. 14A and 14B indicate N15m3 induces a rapid cell death in B6 BMDMs. B6 BMDMs were infected with WT, N15m1, or N15m3 virus at an MOI of 0.1.
Figure 14B:
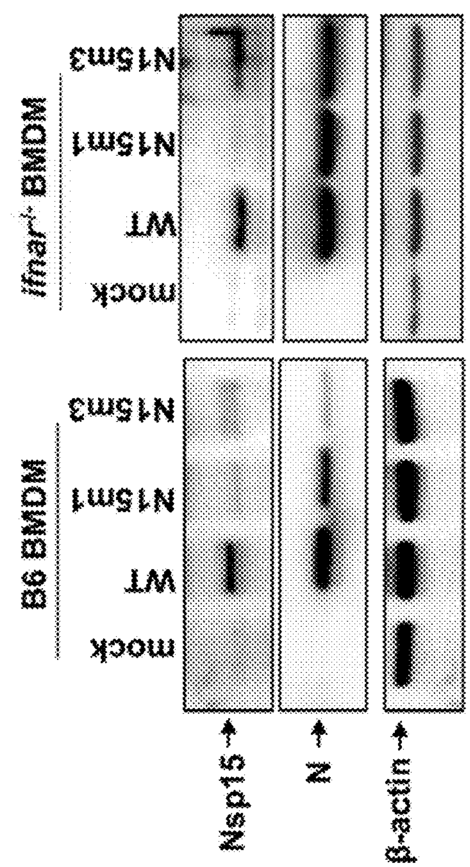

Since T98M mutation causes loss of protein and impairs endoribonuclease activity of nsp15, experiments were performed to determine whether endoribonuclease activity is critical for evasion of host dsRNA sensors. A mutant virus with an endonucleolytic inactive form of nsp15 (H262A), designated as N15m3, was generated. It was found that infection of macrophages with N15m3 resulted in elevated transcription of IFN-α (FIG. 6A), replication deficiency in B6 but not in ifnar$^{-/-}$ BMDMs (FIG. 6B), rapid apoptotic cell death (FIGS. 6C and 14A), and rRNA degradation (FIG. 6D), demonstrating that N15m3 phenocopies N15m1 virus. The H262A mutation did not affect the steady-state level of nsp15 since N15m3, unlike N15m1, expressed similar levels of nsp15 as WT virus in ifnar$^{-/-}$ BMDMs (FIG. 14B). Thus, it was determined that the loss of endoribonuclease activity (H262A) recapitulates the phenotypes associated with the loss of nsp15 protein by T98M mutation. Overall, these results indicated that nsp15 endoribonuclease activity is important for evasion of host dsRNA sensors.

Figure 15A:
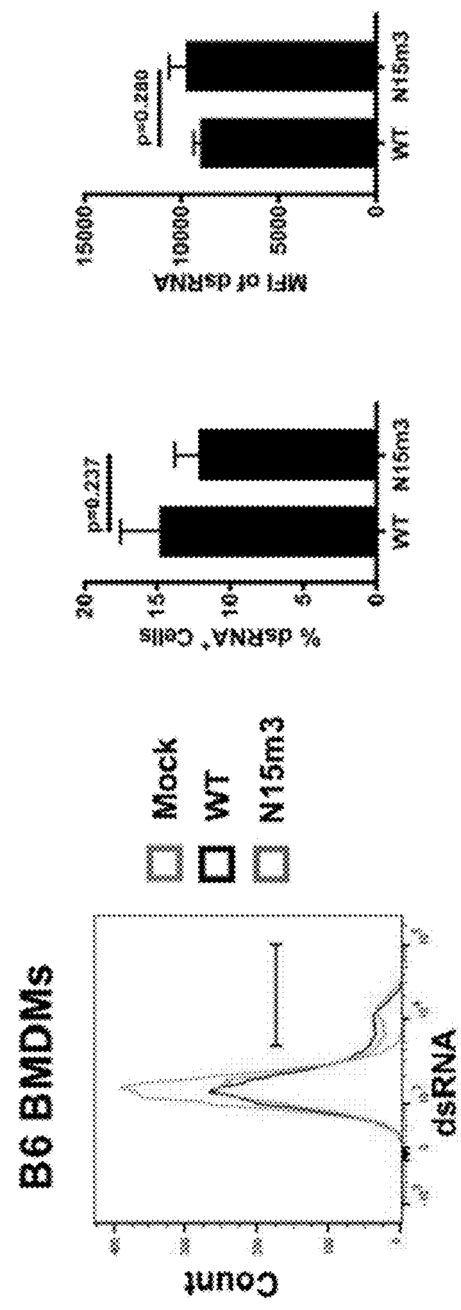
FIGS. 15A and 15B indicate Nsp15 endonuclease activity does not alter the amount of dsRNA in infected BMDMs. B6 (FIG. 15A) or ifnar$^{-/-}$ BMDMs (FIG. 15B) were infected with WT or N15m3 virus at an MOI of 0.1. At 6 hpi, cells were stained for dsRNA and analyzed by flow cytometry.
Figure 15B:
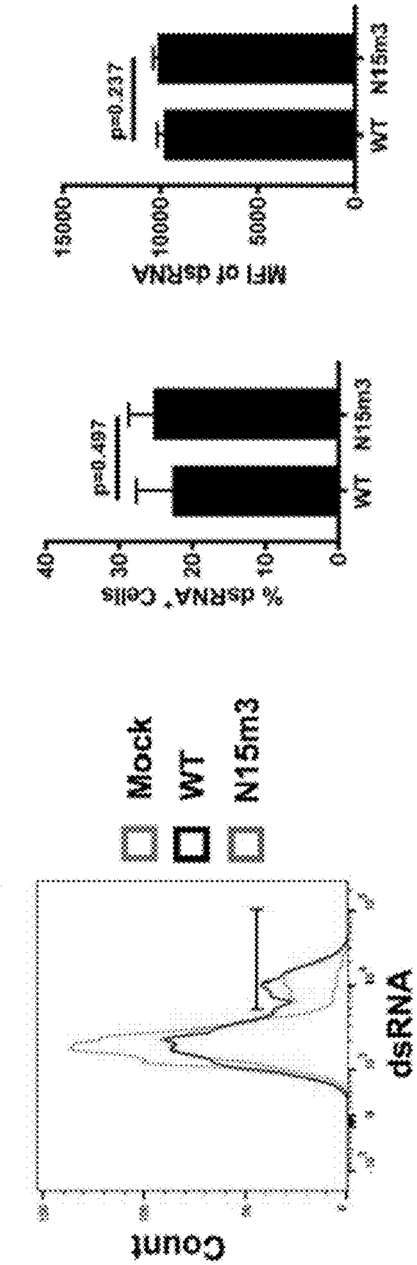

Purified MHV nsp15 from *E. coli* exhibits endonuclease activity in the presence of manganese and the substitution of the catalytic Histidine 262 with Alanine (H262A) resulted in an inactive enzyme. Therefore, the N15m3 virus was chosen as it harbors the catalytic inactive form of nsp15 (H262A) to further determine the role of endoribonuclease activity in preventing the activation of host dsRNA sensors. As CoV infection produces dsRNA intermediates during virus replication, it was hypothesized that nsp15 may degrade viral dsRNA to prevent the accumulation of dsRNA. To test this hypothesis, either B6 or ifnar$^{-/-}$ BMDMs were infected with WT or N15m3 virus and the level of dsRNA was measured. Surprisingly, an increased level of dsRNA in N15m3-infected cells as measured by the fluorescence intensity of dsRNA or the percentage of dsRNA positive cells using flow cytometry (FIG. 15) was not observed, implying that the antagonistic function of nsp15 may not be mediated through degradation of viral dsRNA.

Figure 7A:
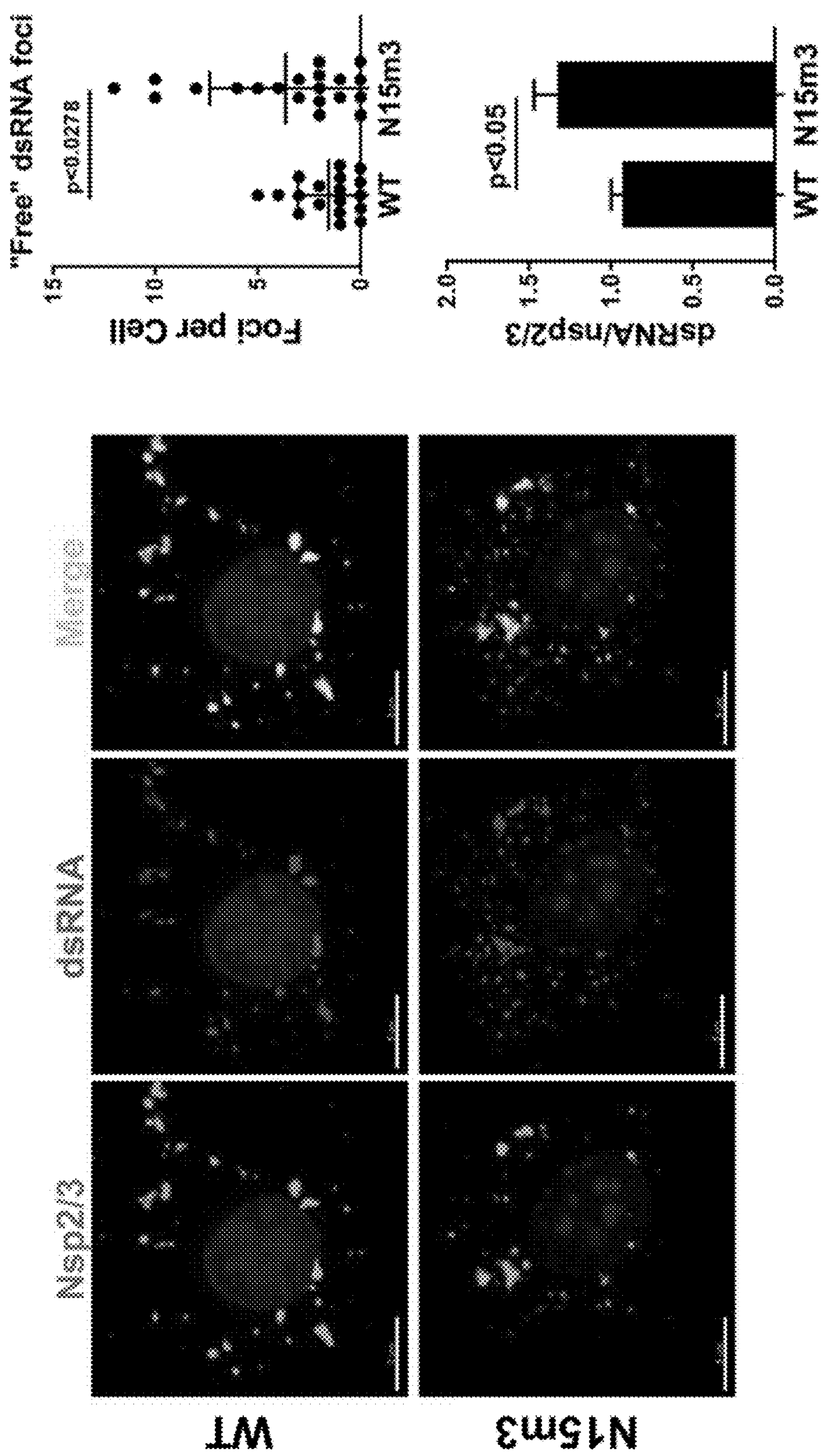
FIGS. 7A and 7B indicate mutation of Nsp15 affects dsRNA distribution in virus-infected BMDMs.

It was believed that CoV dsRNA mainly associates with replication complex and is buried in DMVs, which are thought to protect viral RNA from host sensors. Therefore, it was hypothesized that nsp15 may function to maintain the association of dsRNA with the replication complex or to facilitate dsRNA packing into DMVs. Thus, it was predicted that the nsp15 mutant virus may generate more "free" dsRNAs, and that these free dsRNAs activate host sensors. To test this hypothesis, the subcellular localization of dsRNA and replication complex (nsp2/3 as an indicator) was evaluated by immunofluorescence using specific antibodies. Interestingly, it was found that N15m3 infection yielded more dsRNA foci that did not co-localize with nsp2/3, particularly in ifnar$^{-/-}$ BMDMs (FIG. 7A).

Figure 6B:
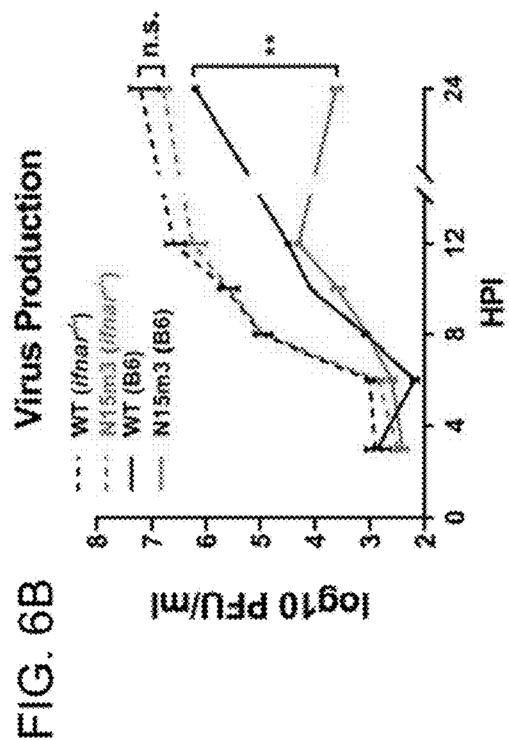
Figure 6C:
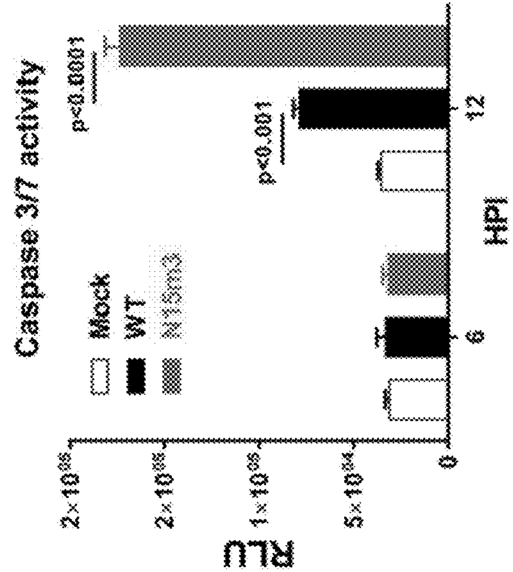
Figure 6D:
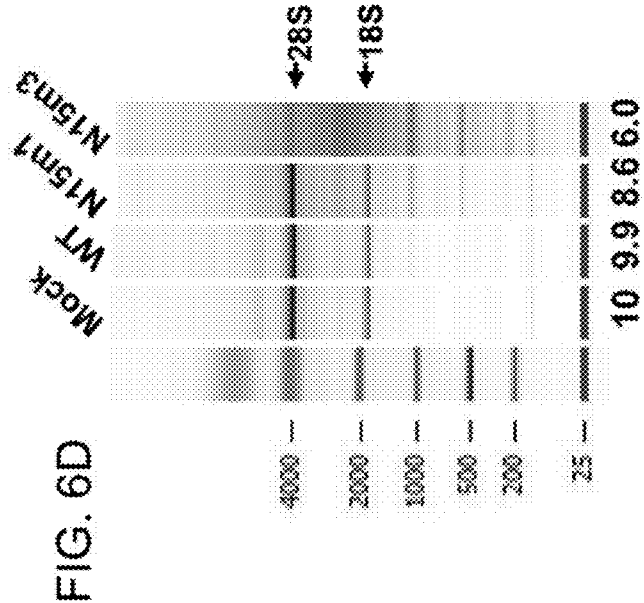
Figure 16A:
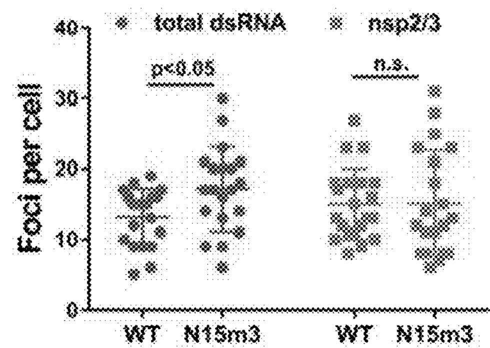
FIGS. 16A and 16B indicate Nsp15 affects the distribution of dsRNA in infected BMDMs. BMDMs were infected with WT or N15m3 at MOI of 0.1. Cells were fixed at 6 hpi and stained with anti-dsRNA, anti-nsp2/3, and Hoescht 33342. The number of foci from 25 images was counted using IMARIS software program.
Figure 16B:
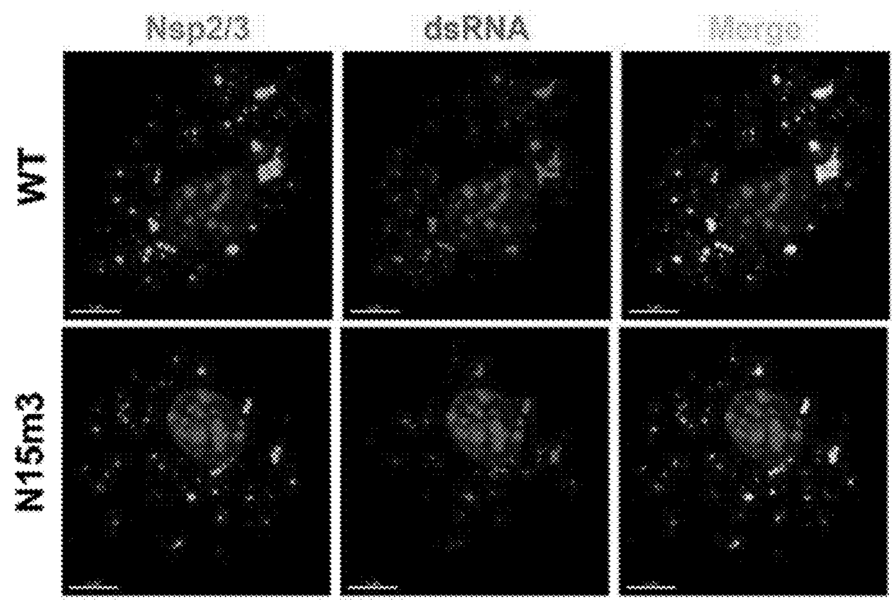
Figure 16B:
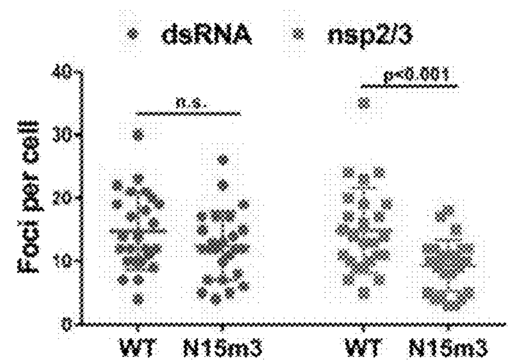
Figure 16B:
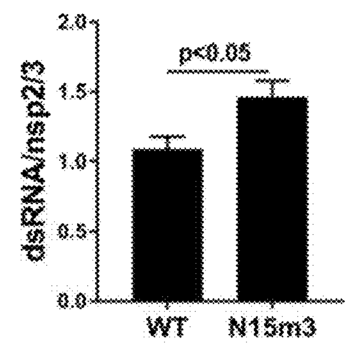

To quantify the "free" dsRNA, the number of foci of dsRNA and nsp2/3 was counted using the IMARIS software program. It was found that in the case of having similar numbers of nsp2/3 foci in ifnar$^{-/-}$ BMDMs, N15m3 produced more dsRNA foci than the WT virus (FIG. 7A left panel and 16A). The number of "free" dsRNA foci and the ratio of dsRNA/nsp2/3 of N15m3 were significantly higher than that of the WT virus (FIG. 7A right panel). In B6 BMDMs, N15m3 virus produced similar numbers of dsRNA foci but significantly less nsp2/3 foci due to the impaired replication (FIG. 6B). It was observed that the ratio of dsRNA/nsp2/3 was still higher in N15m3 than in WT virus (FIG. 16B), consistent with the results obtained from ifnar$^{-/-}$ BMDMs (FIG. 7A). Taken together, these data suggest that nsp15 may not affect the amount of dsRNA in the cell, but does function to maintain the association of dsRNA with nsp2/3, and later dsRNA packing into DMVs.

Figure 7B:
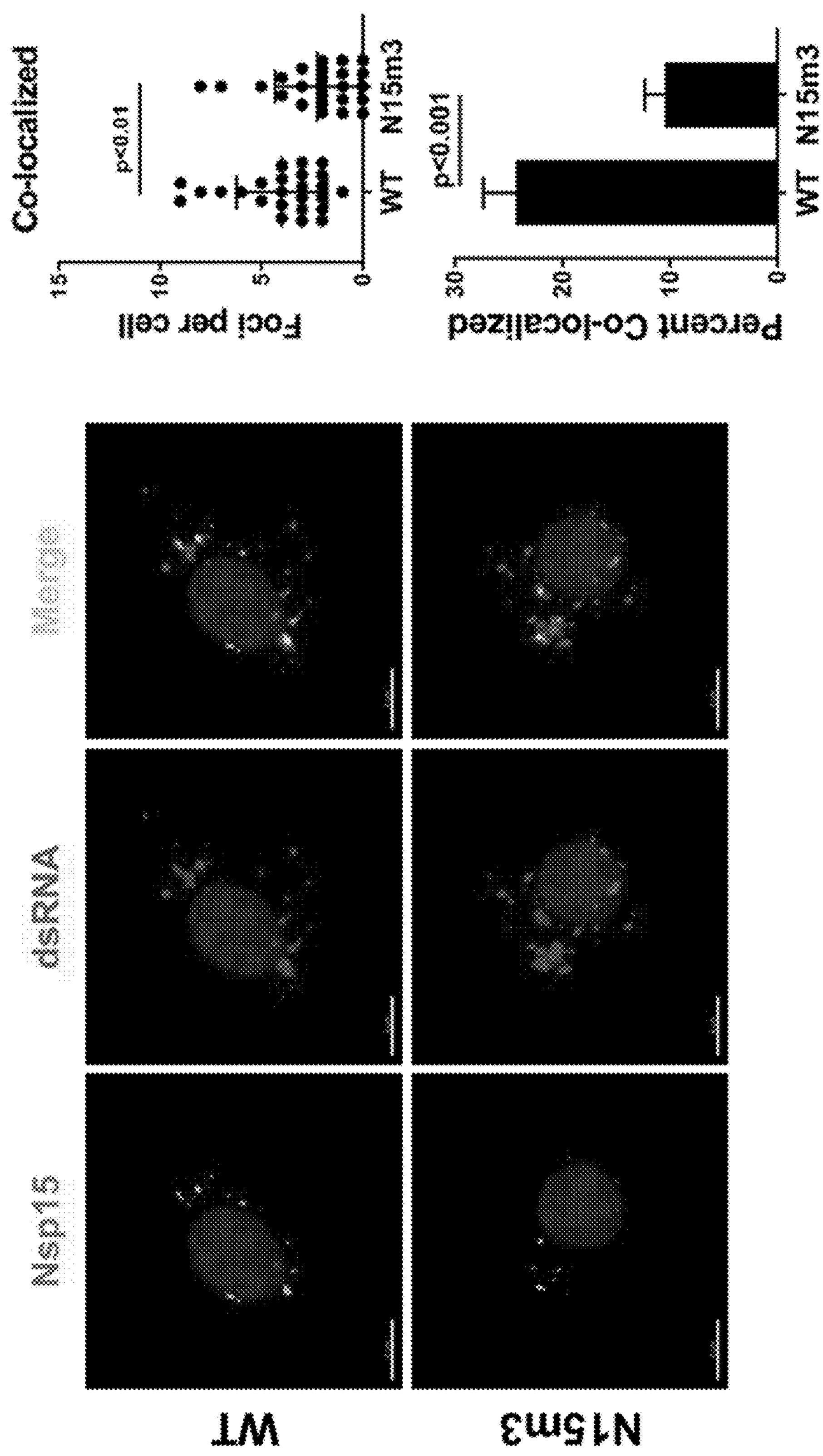

To further understand the relationship between nsp15 and dsRNA, localizations of nsp15 and dsRNA were examined. It was believed that nsp15 associates with newly synthesized viral RNA in characteristic puncta that contain viral replicase proteins, and are considered to be the sites for viral RNA synthesis. Nsp15 and dsRNA were visualized by immunofluorescence using specific antibodies. It was found that the number of dsRNA foci that co-localized with nsp15 was significantly reduced in N15m3-infected cells as compared to WT infected cells (FIG. 7B). These results further supported that nsp15 may associate with dsRNA and the viral replication complex. Therefore, it was concluded that loss of endoribonuclease activity may disrupt the association of dsRNA and replication complex, resulting in more "free" dsRNA to be sensed by host sensors.

Figure 8A:
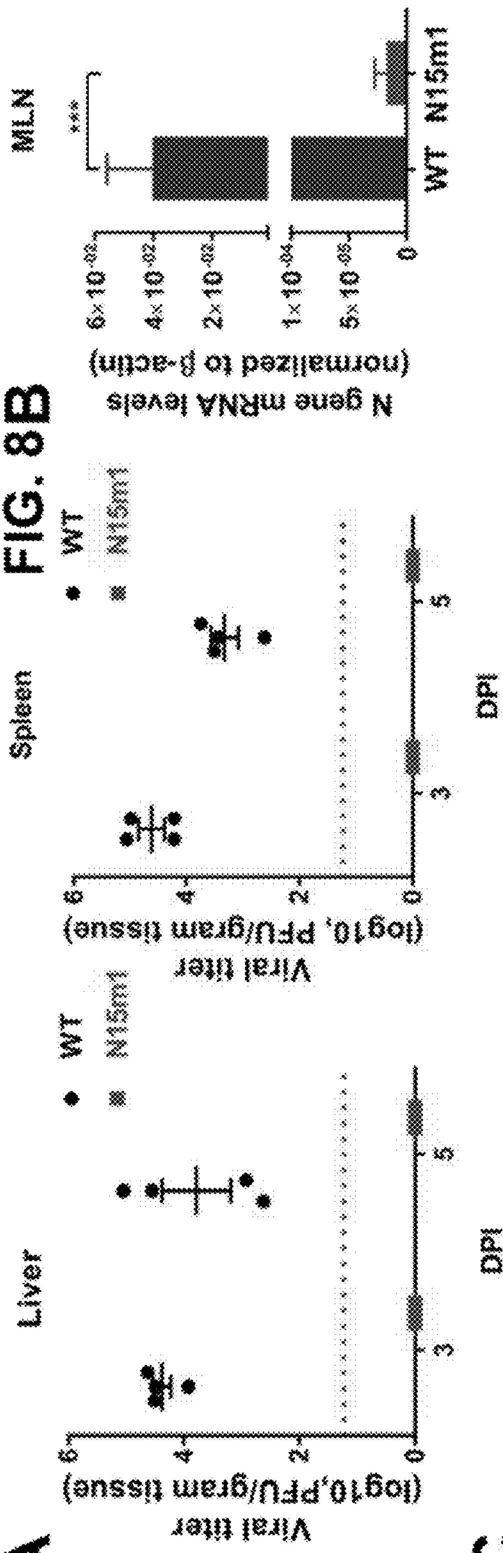
Figure 8B:
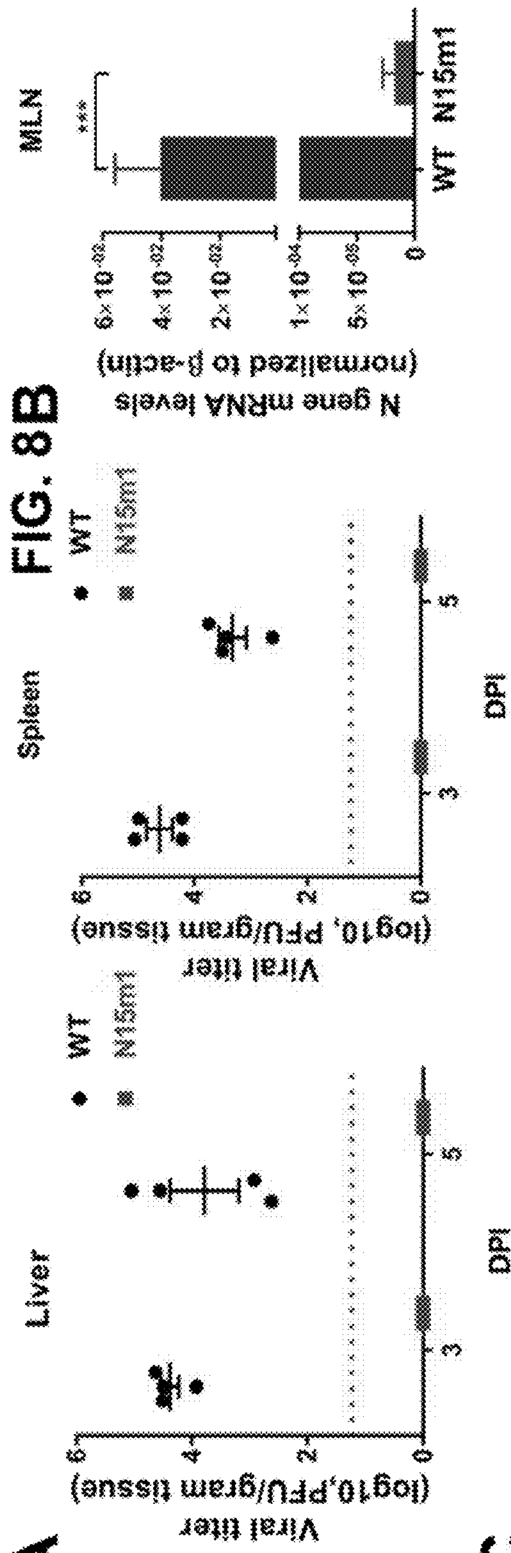
Figure 8C:
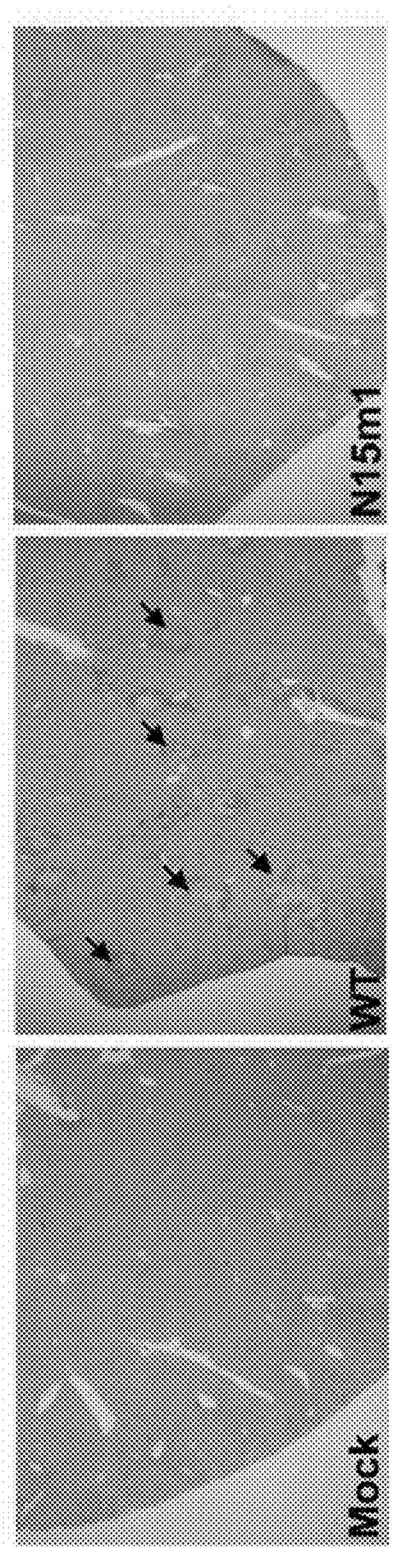
Figure 17A:
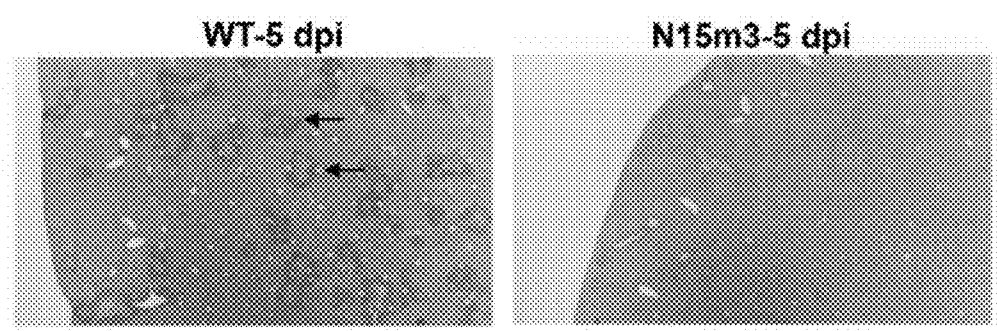
FIGS. 17A and 17B indicate Nsp15 mutant viruses are attenuated in C57BL/6 mice but not in ifnar$^{-/-}$ mice. Six-week old C57BL/6 Mice (n=5) were intraperitoneally inoculated with 6.0×104 PFU virus. At 5 dpi, liver pathology was determined by H&E staining (FIG. 17A). Liver were harvested at 3 and 5 dpi and tested for viral titer by plaque assay using 17Cl-1 cells (FIG. 17B). Red dashed line indicates the limit of detection.

Since nsp15 mutant viruses induce a robust interferon response and activate host dsRNA sensors, additional investigations were performed to determine if the loss of nsp15-mediated antagonism of innate immune responses alters the pathogenesis of murine coronavirus. To this end, a non-lethal model of infection was employed in which WT MHV-A59 titers were expected to peak at day five post-infection. Mice were injected intraperitoneally with 60,000 PFU and the livers and spleens were harvested at days three and five post-infection to measure viral replication. Interestingly, a standard plaque assay to enumerate infectious particles was negative for virus in mice inoculated with N15m1 (FIG. 8A). The more sensitive RT-qPCR assay to detect MHV N gene mRNA identified minimal levels of N15m1 RNA in the mesenteric lymph node (MLN) at day one post-infection but not at later times (FIG. 8B and data not shown). Histological examination of the livers revealed typical lesions associated with infection by WT MHV, but not in N15m1-infected mice (FIG. 8C). Similarly, N15m3-infected mice showed no signs of liver pathology similar to N15m1-infected mice (FIG. 17A).

Figure 17B:
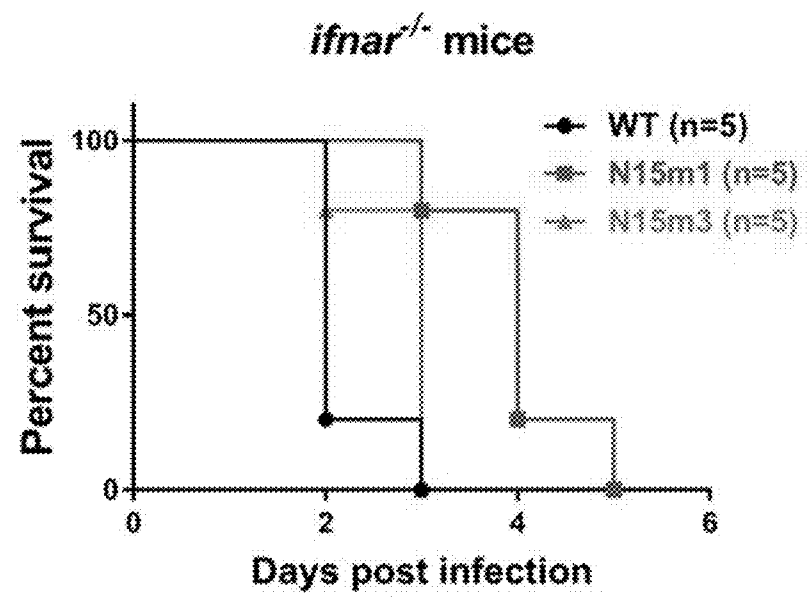

A lethal challenge model was used to determine whether the N15m1 virus was attenuated. Only 600 PFU of WT virus introduced into a mouse cranium is needed to induce lethal encephalitis. The WT-infected mice lost body weight and succumbed to infection by day seven post-infection. In contrast, all N15m1-infected mice survived the infection, exhibiting only transient weight loss at day one post-infection, and gained weight over time (FIG. 8D & 8E). These data reveal that N15m1 is profoundly attenuated and exhibits no pathogenesis even in this sensitive in vivo model. Moreover, ifnar$^{-/-}$ mice were intraperitoneally infected with 50 PFU of either WT or mutant viruses, and all mice rapidly succumbed to infection, supporting the concept that the loss of IFN antagonism function of nsp15 in the mutant viruses is responsible for attenuation during infection of B6 mice (FIG. 17B). Importantly, inoculation with N15m1 fully protected mice from a challenge with 6000 PFU (10-fold lethal dose) of WT MHV (FIG. 8F & 8G).

Overall, these experimental investigations demonstrated the role of nsp15 during WT virus infection in preventing viral dsRNA from activating host sensors. Loss of nsp15 during viral replication resulted in rapid sensing of dsRNA, activation of type I interferon, 2'5'-OAS/RNaseL and PKR, which limits viral replication, dissemination and disease. It was shown that in the absence of IFN signaling, nsp15 mutant viruses replicate similarly as WT virus, indicating that nsp15 endoribonuclease activity is not required for viral RNA synthesis. Instead, nsp15 is critical for derailing the innate immune response to coronavirus replication in macrophages.

The effect of nsp15 as an antagonist of dsRNA sensors is distinct from previous studies of coronavirus replicase-encoded antagonists. CoVs encode a 2'O-methyltransferase (nsp16) to provide a cap structure at the 5' ends of their mRNA to evade host PRRs recognition. SARS-CoV and MHV mutant viruses that lack 2'O-methyltransferase activity triggered the type I IFN response and were attenuated in macrophages and in mice. SARS-CoV and MHV nspl can prevent IFN induction by degrading the host mRNA; however, infection of macrophages with an nspl deletion mutant did not alter IFN induction, but rather, was attenuated in B6 mice. CoVs encode an essential papain-like protease (PLP2 or PLpro) domain within nsp3, which can dysregulate innate immune response by cleaving ubiquitin molecules from cellular substrates. Since nsp15 is highly conserved in all coronaviruses, including relatively benign coronaviruses such as HCoV-229E and OC43, which cause common colds, it is possible that nsp15 is fundamental to the ability of the virus to prevent the recognition of host dsRNA sensors in macrophages allowing for dissemination of the virus to target organs.

Previous studies have shown that coronaviruses encode viral factors to impede the dsRNA-mediated activation of host sensors, such as OAS/RNase L system and PKR. For example, the strain of murine coronavirus used in the above noted investigations also encodes accessary protein ns2, which is another important antagonist of the OAS/RNase L system. Ns2 encodes a 2',5'-phosphodiesterase (PDE) enzyme, which cleaves 2',5'-oligoadenylate, the product of OAS, to prevent RNase L-mediated rRNA degradation in macrophages. Interestingly, coronavirus ns2 confers a liver-specific effect as intracranial infection with the ns2 mutant virus remains lethal. It was found that the nsp15 mutant viruses with an intact ns2 were able to induce rRNA degradation in macrophages and were highly attenuated in both hepatitis and encephalitis mouse models. Investigations of the accessory proteins of MERS-CoV revealed that NS4b has a similar PDE activity as MHV ns2 and inhibits RNase L activity. MERS-CoV NS4a encodes a dsRNA-binding protein that limits the activation of PKR. Deletion of NS4a in the context of the virus was not sufficient to activate PKR and the generation of a stress response, and therefore, MERS-CoV must have redundant mechanisms to suppress recognition and activation of dsRNA sensors. The results presented here indicate that nsp15 may serve as a conserved viral factor to suppress the activation of dsRNA sensors during CoV infection, and that additional suppression of PKR and/or OAS/RNase L by ns2, NS4a, or NS4b may provide tissue-specific or redundant mechanisms of control that likely contribute to viral pathogenesis.

The exact mechanism(s) nsp15 uses to suppress the activation of viral RNA sensors remains to be determined, particularly concerning the role of the nsp15 endoribonuclease activity in the antagonism of dsRNA sensors. Regarding ribonuclease activity, two viruses encoding ribonuclease activity have been shown to function in suppressing innate immune responses. The pestivirus RNase Ems acts as an enzymatically active decoy receptor that degrades viral RNA in endolysosomal compartments, which limits the exposure of the RNA to host dsRNA sensors. The nucleoprotein from Lassa virus also contains a 3' to 5' exonuclease domain that digests free dsRNA and is essential for suppressing the translocation of interferon regulatory factor three and activation of the host innate immune response system. Thus, it was reasonable to hypothesize that nsp15 may degrade viral dsRNA to prevent the detection by host dsRNA sensors. Nonetheless, increased dsRNA levels were not observed in macrophages infected with nsp15 mutant virus (FIG. 14), suggesting that nsp15 might have specific targets instead of broadly degrading RNA. These investigations showed that nsp15 may maintain the association of dsRNA with the replication complex or mediate DMV packing of dsRNA.

In view of the above, the above-noted investigations provided an understanding the mechanisms used by coronaviruses to effectively modulate the innate immune response in macrophages and provide several new directions for development of therapies targeting nsp15 and development of live-attenuated vaccines. For example, it is believed that subjects may be inoculated against various coronaviruses by application of a vaccine comprising a live-attenuated coronavirus comprising a variant replicase gene encoding polyproteins and causing a change, including mutation(s) or deletion(s), in nsp15 that affects the stability or activity of nsp15, as a particular but nonlimiting example, a protein comprising an amino acid mutation of threonine to methionine at position 98 or catalytic histidine to alanine at position 262. The vaccine may include a pharmaceutically acceptable carrier such as but not limited to water, saline, buffered saline, phosphate buffer, alcohol/aqueous solutions, emulsions or suspensions.

Since nsp15 is highly conserved in all coronaviruses, it is believed that the above-described approach can be extended to generate vaccines for all existing and emerging coronaviruses (Coronavirinae). Therefore, it is believed vaccines can be successfully produced by forming mutations in nsp-15 of various coronaviruses including but not limited to Severe Acute Respiratory Syndrome coronavirus (SARS-CoV), Middle East respiratory syndrome coronavirus (MERS-CoV), human coronaviruses 229E (HCoV-229E), 0C43 (HCoV-0C43), HKU1 (HCoV-HKU1), and NL63 (HCoV-NL63), feline infectious peritonitis virus (FIPV), canine coronavirus (CCoV), infectious bronchitis virus (IBV) of chickens, bovine coronavirus (BoCoV), and porcine coronaviruses including transmissible gastroenteritis virus (TGEV), porcine delta coronavirus (PDCoV), porcine epidemic diarrhea virus (PEDV), porcine respiratory coronavirus (PRCV), and porcine hemagglutinating encephalomyelitis coronavirus (PHE-CoV).

The inactivation of nsp15/EndoU of porcine epidemic diarrhea virus (PEDV) by mutation of an infectious clone results in a virus that replicates efficiently in tissue culture but activates the innate immune response to generate interferons in infected-macrophages (FIG. 9). The inactivation of nsp15/EndoU activity in any coronavirus that infects humans or animals will generate a vaccine strain of the virus. This inactivation allows for rapid activation of interferon in virus-infected macrophages, which can then stimulate the adaptive immune response. This can be demonstrated in multiple species of coronaviruses and results in a virus that stimulates the activation of the innate immune response, for example, the Type I interferon response.

Corroboration of aspects of the study and conclusions discussed above have been published in Deng et al., "Coronavirus nonstructural protein 15 mediates evasion of dsRNA sensors and limits apoptosis in macrophages," Proceedings of the National Academy of Sciences May 2017, 114 (21) E4251-E4260; DOI: 10.1073/pnas.1618310114, and in Kindler et al., "Early endonuclease-mediated evasion of RNA sensing ensures efficient coronavirus replication," PLoS Pathog 13(2): e1006195. doi:10.1371/journal. ppat.1006195 (2017). The entire contents of these two papers are incorporated herein by reference.

Additional details relating to the investigations described herein are provided below as discussions of experimental procedures used during the investigations. Such discussions are not intended to set forth limitations to the scope of the invention, but instead are provided to disclose the scope and particular details of the investigations.

The following discussion describes certain experimental procedures relating to FIGS. 1A through 8G.

Cells, antibodies, and chemicals. Delayed brain tumor (DBT) cells were grown in MEM supplemented with 10% tryptose phosphate broth, 5% heat-inactivated fetal calf serum (FCS), 2% penicillin/streptomycin, and 2% glutamine. BHK-21 cells expressing the MHV receptor (BHK-R) were cultured in DMEM) supplemented with 10% FCS and G418 (0.8 mg/ml) (SV30069, HyClone). The 17Cl-1 cell line was maintained in 5% FCS DMEM. Rabbit anti-nsp2/3 serum (anti-D3) and anti-nsp15 serum (anti-D23). Mouse anti-nucleocapsid (J3.3) was from the University of Wisconsin, Madison. Antibodies purchased commercially: dsRNA (K1, Scicons), ISG54 (PA3845, ThermoFisher), eIF2α (sc-133132) and p-eIF2α (sc-12412) were from Santa Cruz. Chemical inhibitors were from the following sources: pan-caspase inhibitor zVAD (627610, Millipore), Necrostatin-1 (Nec-1) (480065, Millipore), PKR inhibitor C16 (527450, Millipore), staurosporine (ALX-380-014, Enzo Life Sciences) and VX-765 (F7120, UBPbio).

Viruses and deep sequencing. WT MHV strain A59 (GenBank accession #AY910861) was generated by reverse genetics. To generate MHV mutant viruses, nucleotide changes were incorporated into the cDNA fragments of MHV-A59 genome through PCR mutagenesis (primers available upon request). Subsequent generation of virus by reverse genetics was performed. Rescued viruses were plaque-purified, propagated on BHK-R cells, and titrated on 17Cl-1 cells. Mutant viruses were maintained exclusively in BHK-R cells. All virus stock preparations and plaque-purified isolates used in this study were full-genome deep sequenced (Kansas State University diagnostic laboratory).

Infection and mouse experiments. BMDMs in 12- or 24-well plates were infected with indicated viral strains at an MOI of 0.1 or 1 in serum-free media. For growth kinetics analysis, cell culture supernatants were collected at indicated time points and titrated by plaque assay on 17Cl-1 cells. For mouse infection, all experiments were performed using protocols reviewed and approved by the Loyola University Chicago IACUC. For intracranial (i.c.) infections, six-week-old C57BL/6J female mice (Jackson Laboratory) were inoculated with 600 PFU virus and monitored for body weight daily and euthanized when weight loss was over 25% according to the IACUC protocol. For intraperitoneal (i.p.) infection, six-week-old mice were injected with 60,000 PFU and organs were collected at indicated time points. Evidence of liver pathology was determined by H&E staining.

Cell death assays. Cell viability and Caspase 3/7 activity were measured using CellTiter Glo (G7571, Promega) or CaspaseGlo 3/7 (G8091, Promega) respectively, according to the manufacturer's protocol, with modification.

Differential scanning fluorimetry (DSF) assay. DSF was carried out in the Stratagene MX3005P real-time PCR machine. The samples contain 1×SYPRO Orange, 10 μM of the recombinant protein. All samples were heated at a rate of 0.5° C./min, and the fluorescence intensity and Tm (melting temperature) were determined.

RNA cleavage assay. The standard RNA cleavage assay used 1×104 CPM of 5'-end radiolabeled RNA substrate (1 μM final RNA concentration) and 0.026 μM Nsp15 in 50 mM Tris-HCl (pH 7.5), 50 mM KCl, 1 mM dithiothreitol, 5 mM MnCl2 at 30° C. The endoribonuclease reactions were terminated by the addition of a gel-loading buffer that contained 7.5 M urea. Products were separated by electrophoresis in 20% polyacrylamide gels containing 7.5 M urea. Gels were wrapped in plastic and exposed to a PhosphorImager screen for quantification using Molecular Dynamics software.

The following discussion describes certain experimental procedures relating to FIGS. 10A through 17B.

Cells, antibodies, and other reagents. Delayed brain tumor (DBT) cells were grown in minimal essential medium (MEM) (61100-061, Gibco) supplemented with 10% tryptose phosphate broth, 5% heat-inactivated fetal calf serum (FCS), 2% penicillin/streptomycin, and 2% glutamine. Baby hamster kidney 21 cells expressing the MHV receptor (BHK-R) were cultured in Dulbecco's modified Eagle medium (DMEM) (12100-046, Gibco) supplemented with 10% heat-inactivated FCS and G418 (0.8 mg/ml) (SV30069, HyClone) to maintain selection for MHV receptor expression. The 17Cl-1 cell line was maintained in 5% FCS DMEM. WT MHV strain A59 (GenBank accession #AY910861) was generated by reverse genetics and full-genome sequenced. Differentiated (see below) bone marrow-derived macrophages (BMDMs) were maintained in bone marrow macrophage (BMM) media containing DMEM (10-017-CV, Corning) supplemented with 30% L929 cell supernatant, 20% FCS, 1% L-glutamine, 1% sodium pyruvate, and 1% penicillin/streptomycin. Rabbit anti-nsp2/3 serum (anti-D3) and anti-nsp15 serum (anti-D23). Mouse anti-nucleocapsid (J3.3) was from the University of Wisconsin, Madison. Antibodies purchased commercially: mouse anti-βactin (A00702, Genscript), mouse anti-calnexin (610523, BD), donkey anti-rabbit-HRP (711-035-152, Jackson ImmunoResearch), goat anti-mouse-HRP (1010-05, SouthernBiotech), dsRNA (K1, Scicons), ISG54 (PA3845, ThermoFisher), elF2α (sc-133132) and p-eIF2α (sc-12412) were from Santa Cruz. Chemical inhibitors were from the following sources: pan-caspase inhibitor zVAD (627610, Millipore), Necrostatin-1 (Nec-1) (480065, Millipore), PKR inhibitor C16 (527450, Millipore), and VX-765 (F7120, UBPbio).

Generation of bone marrow-derived macrophage. Bone marrow was collected from femurs of C57BL/6J (000664, Jackson Labs) or ifnar$^{-/-}$ mice obtained from Washington University in St. Louis. $5\times10^6$ bone marrow cells were plated in 100×26 mm petri dishes (25387-030, VWR) with 15 mL BMM media with 50 μM β-mercaptoethanol. After 3 days of incubation at 37° C./5% $CO_2$, 10 mL of BMM media was added. Following another 3 days of differentiation, BMDMs were washed in cold 1×PBS, incubated for 30 min at 4° C. in 10 mL 1×PBS then gently rinsed from the plates by manual pipetting. $1\times10^7$ cells/mL were suspended in BMM media with 10% DMSO and stored in liquid nitrogen liquid phase until use. For preparation of L929 cell supernatant, $3.75\times10^5$ L929 cells were plated in 75 mL medium (DMEM [10-017-CV, Corning], 10% FCS, 1% L-glutamine, 1% sodium pyruvate, 1% nonessential amino acids, and 1% penicillin/streptomycin) in a T150 flask (10-126-34, Thermofisher). After 6 days of incubation at 37° C./5% $CO_2$, the supernatant was harvested, filtered, and stored at −20° C. until use. For viral infections, BMDMs were thawed and plated in 100×26 mm petri dishes in BMM media without β-mercaptoethanol. After 3 days of incubation at 37° C. /5% $CO_2$, cells were plated onto tissue culture dishes for subsequent infection experiments after 24-hour incubation.

Mutant viruses and deep sequencing. To generate MHV mutant viruses, nucleotide changes were incorporated into the MHV-A59 genome through PCR mutagenesis (primers available upon request) of cDNA fragments. Subsequent generation of virus by reverse genetics was performed. Viral genomic RNA from in vitro transcription (mMESSAGE mMACHINE T7 Transcription Kit; AM1344, Invitrogen Ambion) of ligated cDNA fragments was electroporated into BHK-R cells. Cell supernatant was collected as viral stock following observation of cytopathic effects. Infectious clones were plaque-purified, propagated on BHK-R cells, and titrated on 17Cl-1 cells. Mutant viruses were maintained exclusively in BHK-R cells, which do not produce or respond to interferon. All virus stock preparations and plaque-purified isolates used in this study were full-genome deep sequenced (Kansas State University diagnostic laboratory). Briefly, viral RNA was extracted from virus stocks using QIAamp MinElute Virus Spin Kit (57704, QIAGEN), used to generate a cDNA Library and sequenced by Miseq or Ion Torrent technology. Mutant MHV sequences were aligned to the wild-type MHV-A59 synthetic construct (GenBank accession #AY910861).

Evaluating viral replication by plaque assay. To determine virus growth kinetics, BMDMs in 24-wells plates were infected with indicated viral strains at an MOI of 0.1 in serum-free media. After 1 h incubation, inoculum was replaced with fresh, complete medium. Cell culture supernatants were collected at indicated time points and titrated by plaque assay on 17Cl-1 cells. To determine the viral titer in organs, a portion of tissue was homogenized with 1.0 mm dia. zirconia/silicon beads (11079110z, BioSpec Products) using an automated homogenizer (6.0 m/sec, 40 sec duration) (MP Biomedicals) in serum-free DMEM. The homogenized organs were centrifuged at 10,000×g for 5 min and the clarified supernatants were titrated for viral plaques on 17Cl-1 cells. Titers were obtained from three independent assays for each sample. Graphs of virus kinetics were generated using Prism 7 software (GraphPad Software, Inc.).

Cell death assays. Cell viability and Caspase 3/7 activity were measured using CellTiter Glo (G7571, Promega) or CaspaseGlo 3/7 (G8091, Promega) respectively, according to the manufacturer's protocol, with modification. Briefly, $3.0\times10^5$ BMDMs/well were plated in 24-well plates and infected at an MOI of 0.1 for 1 h in serum-free media. Media was replaced with complete media, or for addition of chemical inhibitors, viral inoculum was replaced with completed BMM media containing indicated concentration of inhibitors. Infected BMDMs were incubated for 24h at 37° C./5% $CO_2$. BMDMs were washed twice with 1×PBS and lysed with 100 μL Glo reagent/medium mixture (1:1). 50 μL of cell lysate was used for measuring the luminescence signal. Standard deviation and unpaired t test were performed on technical triplicates and data are representative of three independent experiments. Graphs of cell viability were generated using Prism 7 software (GraphPad Software, Inc.).

Immunofluorescence. BMDMs ($1.5\times10^5$ cell/well) were plated on a glass coverslip in a 24-well plate for 24 h and subsequently infected with wild-type or mutant virus at an MOI of 0.1 in serum-free media. At 6 or 12 hpi, the infected cells were fixed with 4% formaldehyde in 0.095 M PIPES buffer (P1851, Sigma), permeabilized with 0.1% Triton X-100 (T8787, Sigma) in 1×PBS, and blocked with 2% BSA. Primary and secondary antibodies were used as follows: anti-NSP2/3 (1:1500), anti-dsRNA (1:500), anti-ISG54 (1:500), anti-nucleocapsid (1:500), donkey anti-rabbit IgG alexafluor 488 (1:1000) (A-21441, Invitrogen), and goat anti-mouse IgG Alexa Fluor 568 (1:1000) (A11004, Thermofisher). Nuclei were visualized with Hoescht 33342 (1:2500) (H1339, Life Technologies). Cells were imaged by collecting Z-stack images with a Deltavision wide field fluorescent microscope (Applied Precision, GE) equipped with a digital camera (CoolSNAP HQ, Photometrics). Images were taken with a 20× or 100× lens. Samples were excited with light generated by an Insight SSI solid state illumination module (Applied Precision, GE) and deconvolved with SoftWoRx deconvolution software (Applied Precision, GE). All images were collected under identical acquisition conditions and processed using Imaris 7.6.4 (Bitplane).

FACS analysis. BMDMs ($6.0\times10^5$) were plated in a 12-well plate (Corning) for 24 h and subsequently infected with wild-type or mutant virus at an MOI of 0.1. At 6 hpi, cells were collected and fixed with 4% formaldehyde in 1×PBS, permeabilized with 0.1% Triton X-100 in 1×PBS, and blocked with 1×PBS containing 2% FCS and 0.5% sodium azide. Cells were labelled with fixable viability dye (65-0865-14, eBioscience) and antibodies against indicated primary and secondary antibodies, donkey anti-rabbit alexafluor 488 and goat anti-mouse primary antibody labeled with Alexa Fluor 568. Cells were analyzed using a LSR Fortessa cell analyzer (BD Bioscience). Flow cytometry data were analyzed using FlowJo software (Treestar).

Quantification of IFN-α production by reverse transcription quantitative PCR (RT-qPCR) and ELISA. BMDMs in a 12 or 24-well plate were mock-infected or infected with virus at an MOI of 0.1 or 1. At indicated time points, monolayer cells were used for RNA extraction using an RNeasy Mini Kit (74104, QIAGEN), while cell culture supernatants were collected for ELISA. To determine IFN-α11, beta-actin or MHV-A59 N gene mRNA production, total RNAs were extracted and an equal amount of RNA (~1 μg) was used for cDNA synthesis using Rte HT First Strand Kit (330401, QIAGEN). Quantitative PCR was performed with specific primers for mouse IFN-α11 (PPM03050B-200, QIAGEN), mouse β-actin (PPM02945B-200, QIAGEN) or MHV-A59 N gene using $RT^2$ SYBR Green qPCR Mastermix (330502, QIAGEN) in the Bio-Rad CFX96 system. Thermocycler was set as follows: one step at 95° C. (10 min), 40 cycles of 95° C. (15 s), 60° C. (1 min) and plate read, one step at 95° C. (10 s) and a melt curve from 65° C.-95° C. at increments of 0.5° C./0.05s. Samples were evaluated in triplicate and data are representative of 3 independent experiments. To measure secreted IFN-α, 50 μL cell culture supernatant was used for assay using a mouse IFN-α ELISA kit (BMS6027, eBioscience) as per the manufacturer's instruction. Graphs were generated using Prism 7 software (GraphPad Software, Inc.).

Electron microscopy. $6.0\times10^5$ B6 BMDMs were plated per well in a 12-well plate (Corning) in 1 mL BMM media. After 24 h, cells were infected with virus at 0.1 MOI in serum-free DMEM. Control cells were treated with BMM media. Following a 1 h incubation at 37° C./5% $CO_2$, media was replaced with BMM media. Uninfected controls were treated with 1 μM staurosporine (ALX-380-014, Enzo Life Sciences) prepared in BMM media to induce apoptosis. Cells were further incubated at 37° C./5% $CO_2$ for 16 h then prepped for EM. Cells were washed in 1×PBS then incubated for 30 min at 4° C. in 1×PBS. Cells were gently collected from plates using a pipette, pelleted at 1200 rpm for 5 min at 4° C. and fixed (4% glutaraldehyde in 0.1 M cacodylate buffer). Cell sections were prepared and imaged by the Electron Microscopy Core Facility at Loyola University Chicago, Maywood, Ill.

Western blotting. 12-well plates (Corning) containing $6.0\times10^5$ B6 BMDMs/well in BMM media were media-treated or infected with virus at 0.1 MOI in serum-free DMEM for 1 hour at 37° C./5% $CO_2$. Media was replaced with fresh BMM media and cells were returned to the incubator. After 6, 12 or 24 hours, cells were lysed in 100 μL cold lysis buffer (20 mM tris pH 7.5, 150 mM NaCl, 1 mM EGTA, 1 mM EDTA, 1% Triton X-100, 2.5 mM sodium pyrophosphate, 1 mM β-glycerophosphate, 1 mM sodium ortho-vanadate, 1 μg/mL leupeptin, 1 mM PSMF) and scraped into tubes. Cells in lysis buffer were incubated on ice for 10 min then pelleted at 14,000 rpm for 10 min at 4° C. Cell-free supernatant was diluted in 2×sample buffer (10% glycerol, 5% β-ME, 3% SDS, 7.5 mg/mL Trizma-base, bromophenol blue). Samples were separated by electrophoresis through 12% acrylamide PAGE-gel and transferred to PVDF Immuno-Blot membranes (162-0177, Bio-Rad) using the semi-dry transfer system (Bio-Rad). Membranes were suspended in blocking buffer, containing 5% w/v nonfat dry milk in 1×TBST (Tris-buffered saline+1% Tween-20), for 1.5 h at RT. To detect activated caspase-3, rabbit monoclonal antibody to cleaved caspase-3 (Asp175; Cell Signaling Technology) was applied (1:1000) overnight at 4° C. with gentle shaking. A second set of membranes, used to determine cell protein expression via mouse anti-βactin (1:5000) or relative virus replication via mouse-anti-J3.3 N protein (1:200), were incubated for 1.5 h at RT. All membranes were washed three times in 1×TBST and secondary antibody, donkey anti-rabbit-HRP (1:2500) for caspase-3 monoclonal or goat anti-mouse-HRP (1:5000) for N protein and β-actin, was applied for 1.5 h at RT with gentle shaking. Membranes were washed three times with 1×TBST and chemiluminescence was visualized using Western Lightning Plus-ECL reagent (50-904-9326, PerkinElmer, Inc.).

Purification of the recombinant MHV Nsp15 protein from *E. coli*. The cDNA sequences of WT MHV Nsp15 and T98M were amplified using the appropriate primers and subcloned into the pET-His-SUMO vector using the fusion PCR. The constructs harboring the WT Nsp15 or T98M mutant gene were transformed into Rosetta (DE3) pLys cells. A single colony was inoculated in 100 mL of Terrific Broth (TB) in the presence of 50 μg/mL of ampicillin and 17 μg/mL chloramphenicol and incubated at 37° C. overnight. The culture was then transferred into 3 L of TB media and cultured until the $OD_{600}$ reached 0.8. The temperature was decreased to 16° C. and IPTG was added to a final concentration of 0.2 mM for 20 h. The cells were collected by centrifugation at 8000×g for 10 min and cell pellets were suspended in lysis buffer containing 10% glycerol, 50 mM HEPES (pH 7.0), 400 mM NaCl, 5 mM β-ME and 10 mM imidazole. The lysate was centrifuged at 15,000×g for 30 min and the supernatant was loaded onto a Ni-NTA column. The Ni-NTA column was subsequently washed three times with lysis buffer containing 20 mM imidazole. The protein was eluted with elution buffer containing 500 mM imidazole and then the buffer was changed to 10% glycerol, 20 mM Tris-Cl (pH 7.5) and 5 mM β-ME. The sample was further purified by Mono Q-Sepharose with a gradient of Tris buffer containing 0 to 1 M NaCl. Nsp15 was quantified by SDS-PAGE compared to a known concentration of BSA, and stored at −80° C. in a buffer containing 10% glycerol, 20 mM Tris-CI, pH 7.5, 300 mM NaCl and 10 mM β-ME.

Dynamic light scattering (DLS). Recombinant MHV Nsp15 or T98M proteins were diluted in storage buffer (10% glycerol, 20 mM Tris-CI, pH 7.5, 300 mM NaCl and 5 mM β-ME) at different concentrations. Size measurement was carried out by Zetasizer Nano-S dynamic light scattering (Malvern Instruments) at RT. Each sample was measured at least three times. The average intensity and size distributions are shown.

Differential scanning fluorimetry (DSF) assay. DSF was carried out in the Stratagene MX3005P real-time PCR machine. The samples contain 1×SYPRO Orange, 10 μM of the recombinant protein. All samples were heated at a rate of 0.5° C./min, and the fluorescence intensity and Tm (melting temperature) were determined.

Bioanalyzer RNA analysis. Equal amounts of total RNA purified from BMDMs were analyzed on an Agilent 2100 Bioanalyzer using RNA Nano LabChips.

Mouse experiments. All experiments were performed using protocols reviewed and approved by the Loyola University Chicago IACUC. C57BL/6J mice were purchased from Jackson Laboratory. For intracranial (i.c.) infections, six-week-old mice were inoculated with 600 PFU in 20 μL of WT or mutant MHV. Infected mice were monitored for body weight daily and euthanized when weight loss was over 25% according to the IACUC protocol. Graphs of survival rate were generated using Prism 7 software (GraphPad Software, Inc.). Statistical analysis of survival rate was conducted with log rank test. For intraperitoneal (i.p.) infection, six-week-old mice were injected with 60,000 PFU in 100 μL 1×PBS. Organs were collected at indicated time points and evaluated for viral replication. Evidence of viral pathogenesis was determined by H&E staining.

Sequence alignment. Nsp15 T98 region from representative strains of coronavirus sub-groups using Clustal W. Alpha-coronavirus: NL63 (Amsterdam I strain, AY567487), PEDV (CV777 strain, NC_003436); beta-coronavirus: MHV, (A59 strain, AY910861); SARS-CoV (MA15 strain, FJ882957); MERS-CoV (EMC strain, JX869059); gamma-coronavirus: IBV (Beaudette strain, NC_001451); delta-coronavirus: PDCoV (KJ567050).

While the invention has been described in terms of specific or particular embodiments and investigations, it should be apparent that alternatives could be adopted by one skilled in the art. For example, the specific mutated coronavirus could differ from that described or could have additional mutations. Accordingly, it should be understood that the invention is not necessarily limited to any embodiment described herein or illustrated in the drawings. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:

1. A method of stimulating production of type I interferon in porcine alveolar macrophages, comprising administering to a porcine subject a composition comprising a live, attenuated porcine epidemic diarrhea virus (PEDV) comprising one or more substitution mutations in a non-structural protein-15 (nsp15), wherein said one or more substitution mutations includes a substitution of a catalytic histidine amino acid that results in a loss of endoribonuclease enzymatic activity, and wherein said PEDV does not comprise a mutation in ExoN.

2. The method according to claim 1, wherein said one or more substitution mutations at a catalytic histidine residue comprises an alanine substitution.

3. The method according to claim 1, wherein said method further comprises determining the amount of type I interferon production.

4. The method according to claim 1, wherein said method further comprises determining a survival rate in a population of porcine subjects.

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Mouse hepatitis virus

<400> SEQUENCE: 1

Glu Gln Arg Lys Gly
1               5

<210> SEQ ID NO 2
<211> LENGTH: 5
<212> TYPE: PRT
<213> ORGANISM: Mouse hepatitis virus

<400> SEQUENCE: 2

Ser Ser Thr Tyr Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Gln Ala Lys Gly
1               5

<210> SEQ ID NO 4
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 4

Ser Ser Met Tyr Lys
1               5


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Gln Ala Lys Gly
1               5


<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Thr Tyr Lys
1               5


<210> SEQ ID NO 7
<211> LENGTH: 12
<212> TYPE: PRT
<213> ORGANISM: Mouse hepatitis virus

<400> SEQUENCE: 7

Phe Cys Ser Ser Thr Tyr Lys Val Cys Lys Tyr Thr
1               5                   10


<210> SEQ ID NO 8
<211> LENGTH: 12
<212> TYPE: PRT
<213> ORGANISM: SARS coronavirus

<400> SEQUENCE: 8

Ala His Val Ser Thr Ile Gly Val Cys Thr Met Thr
1               5                   10


<210> SEQ ID NO 9
<211> LENGTH: 12
<212> TYPE: PRT
<213> ORGANISM: MERS coronavirus

<400> SEQUENCE: 9

Tyr Gly Thr Ala Thr Ile Gly Val Cys Lys Tyr Thr
1               5                   10


<210> SEQ ID NO 10
<211> LENGTH: 12
<212> TYPE: PRT
<213> ORGANISM: Human coronavirus NL63

<400> SEQUENCE: 10

Phe Thr Cys Tyr Thr His Ser Val Cys Lys Tyr Thr
1               5                   10
```

<210> SEQ ID NO 11
<211> LENGTH: 12
<212> TYPE: PRT
<213> ORGANISM: Porcine epidemic diarrhea virus

<400> SEQUENCE: 11

Leu Thr Thr Phe Thr Lys Asp Val Cys Lys Tyr Thr
1 5 10

<210> SEQ ID NO 12
<211> LENGTH: 12
<212> TYPE: PRT
<213> ORGANISM: Infectious bronchitis virus

<400> SEQUENCE: 12

Leu Tyr Arg Asn Thr Val Lys Val Cys Ala Tyr Thr
1 5 10

<210> SEQ ID NO 13
<211> LENGTH: 12
<212> TYPE: PRT
<213> ORGANISM: Porcine delta coronavirus

<400> SEQUENCE: 13

Ile Phe Gln Tyr Thr Ile Asn Val Ser Thr Tyr Thr
1 5 10

<210> SEQ ID NO 14
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
gaagcgaaac ccuaag 16

<210> SEQ ID NO 15
<211> LENGTH: 31365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
gataagagtg attggcgtcc gtacgtaccc tctcaactct aaaactcttg tagtttaaat 60
ctaatctaaa ctttataaac ggcacttcct gcgtgtccat gcccgcgggc ctggtcttgt 120
catagtgctg acatttgtag ttccttgact ttcgttctct gccagtgacg tgtccattcg 180
gcgccagcag cccacccata ggttgcataa tggcaaagat gggcaaatac ggtctcggct 240
tcaaatgggc cccagaattt ccatggatgc ttccgaacgc atcggagaag ttgggtaacc 300
ctgagaggtc agaggaggat gggttttgcc cctctgctgc gcaagaaccg aaagttaaag 360
gaaaaacttt ggttaatcac gtgagggtga attgtagccg gcttccagct ttggaatgct 420
gtgttcagtc tgccataatc cgtgatattt ttgtagatga ggatccccag aaggtggagg 480
cctcaactat gatggcattg cagttcggta gtgccgtctt ggttaagcca tccaagcgct 540
tgtctattca ggcatggact aatttgggtg tgcttcccaa aacagctgcc atggggttgt 600
tcaagcgcgt ctgcctgtgt aacaccaggg agtgctcttg tgacgcccac gtggcctttc 660

```
acctttttac ggtccaaccc gatggtgtat gcctgggtaa tggccgtttt ataggctggt    720
tcgttccagt cacagccata ccggagtatg cgaagcagtg gttgcaaccc tggtccatcc    780
ttcttcgtaa gggtggtaac aaagggtctg tgacatccgg ccacttccgc cgcgctgtta    840
ccatgcctgt gtatgacttt aatgtagagg atgcttgtga ggaggttcat cttaacccga    900
agggtaagta ctcctgcaag gcgtatgctc ttcttaaggg ctatcgcggt gttaagccca    960
tcctgtttgt ggaccagtat ggttgcgact atactggatg tctcgccaag ggtcttgagg   1020
actatggcga tctcaccttg agtgagatga aggagttgtt ccctgtgtgg cgtgactcct   1080
tggatagtga agtccttgtg gcttggcacg ttgatcgaga tcctcgggct gctatgcgtc   1140
tgcagactct tgctactgta cgttgcattg attatgtggg ccaaccgacc gaggatgtgg   1200
tggatggaga tgtggtagtg cgtgagcctg ctcatcttct cgcagccaat gccattgtta   1260
aaagactccc ccgtttggtg gagactatgc tgtatacgga ttcgtccgtt acagaattct   1320
gttataaaac caagctgtgt gaatgcggtt ttatcacgca gtttggctat gtggattgtt   1380
gtggtgacac ctgcgatttt cgtgggtggg ttgccggcaa tatgatggat ggctttccat   1440
gtccagggtg taccaaaaat tatatgccct gggaattgga ggcccagtca tcaggtgtta   1500
taccagaagg aggtgttcta ttcactcaga gcactgatac agtgaatcgt gagtccttta   1560
agctctacgg tcatgctgtt gtgccttttg gttctgctgt gtattggagc ccttgcccag   1620
gtatgtggct tccagtaatt tggtcttctg ttaagtcata ctctggtttg acttatacag   1680
gagtagttgg ttgtaaggca attgttcaag agacagacgc tatatgtcgt tctctgtata   1740
tggattatgt ccagcacaag tgtggcaatc tcgagcagag agctatcctt ggattggacg   1800
atgtctatca tagacagttg cttgtgaata ggggtgacta tagtctcctc cttgagaatg   1860
tggatttgtt tgttaagcgg cgcgctgaat ttgcttgcaa attcgccacc tgtggagatg   1920
gtcttgtacc cctcctacta gatggtttag tgccccgcag ttattatttg attaagagtg   1980
gtcaagcttt cacctctatg atggttaatt ttagccatga ggtgactgac atgtgtatgg   2040
acatggcttt attgttcatg catgatgtta aagtggccac taagtatgtt aagaaggtta   2100
ctggcaaact ggccgtgcgc tttaaagcgt tgggtgtagc cgttgtcaga aaaattactg   2160
aatggtttga tttagccgtg gacattgctg ctagtgccgc tggatggctt tgctaccagc   2220
tggtaaatgg cttatttgca gtggccaatg gtgttataac ctttgtacag gaggtgcctg   2280
agcttgtcaa gaattttgtt gacaagttca aggcattttt caaggttttg atcgactcta   2340
tgtcggtttc tatcttgtct ggacttactg ttgtcaagac tgcctcaaat agggtgtgtc   2400
ttgctggcag taaggtttat gaagttgtgc agaaatcttt gtctgcatat gttatgcctg   2460
tgggttgcag cgaagccact tgtttggtgg gtgagattga acctgcagtt tttgaagatg   2520
atgttgttga tgtggttaaa gccccattaa catatcaagg ctgttgtaag ccacccactt   2580
ctttcgagaa gatttgtatt gtggataaat tgtatatggc caagtgtggt gatcaatttt   2640
accctgtggt tgttgataac gacactgttg gcgtgttaga tcagtgctgg aggtttccct   2700
gtgcgggcaa gaaagtcgag tttaacgaca agcccaaagt caggaagata ccctccaccc   2760
gtaagattaa gatcaccttc gcactggatg cgacctttga tagtgttctt tcgaaggcgt   2820
gttcagagtt tgaagttgat aaagatgtta cattggatga gctgcttgat gttgtgcttg   2880
acgcagttga gagtacgctc agcccttgta aggagcatga tgtgataggc acaaaagttt   2940
gtgctttact tgataggttg gcaggagatt atgtctatct tttgatgagg gaggcgatg    3000
```

```
aagtgatcgc cccgaggatg tattgttcct tttctgctcc tgatgatgaa gactgcgttg   3060

cagcggatgt tgtagatgca gatgaaaacc aagatgatga tgctgaagac tcagcagtcc   3120

ttgtcgctga tacccaagaa gaggacggcg ttgccaaggg gcaggttgag gcggattcgg   3180

aaatttgcgt tgcgcatact ggtagtcaag aagaattggc tgagcctgat gctgtcggat   3240

ctcaaactcc catcgcctct gctgaggaaa ccgaagtcgg agaggcaagc gacagggaag   3300

ggattgctga ggcgaaggca actgtgtgtg ctgatgctgt agatgcctgc cccgatcaag   3360

tggaggcatt tgaaattgaa aaggttgaag actctatctt ggatgagctt caaactgaac   3420

ttaatgcgcc agcggacaag acctatgagg atgtcttggc attcgatgcc gtatgctcag   3480

aggcgttgtc tgcattctat gctgtgccga gtgatgaaac ccactttaaa gtgtgtggat   3540

tctattcgcc tgctatagag cgcactaatt gttggctgcg ttctactttg atagtaatgc   3600

agagtctacc tttggaattt aaagacttgg agatgcaaaa gctctggttg tcttacaagg   3660

ccggctatga ccaatgcttt gtggacaaac tagttaagag cgtgcccaag tctattatcc   3720

ttccacaagg tggttatgtg gcagattttg cctatttctt tctaagccag tgtagcttta   3780

aagcttatgc taactggcgt tgtttagagt gtgacatgga gttaaagctt caaggcttgg   3840

acgccatgtt tttctatggg gacgttgtgt ctcatatgtg caagtgtggt aatagcatga   3900

ccttgttgtc tgcagatata ccctacactt tgcattttgg agtgcgagat gataagtttt   3960

gcgcttttta cacgccaaga aaggtcttta gggctgcttg tgcggtagat gttaatgatt   4020

gtcactctat ggctgtagta gagggcaagc aaattgatgg taaagtggtt accaaattta   4080

ttggtgacaa atttgatttt atggtgggtt acgggatgac atttagtatg tctccttttg   4140

aactcgccca gttatatggt tcatgtataa caccaaatgt ttgttttgtt aaaggagatg   4200

ttataaaggt tgttcgctta gttaatgctg aagtcattgt taaccctgct aatgggcgta   4260

tggctcatgg tgcaggtgtt gcaggtgcta tagctgaaaa ggcgggcagt gcttttatta   4320

aagaaacctc cgatatggtg aaggctcagg gcgtttgcca ggttggtgaa tgctatgaat   4380

ctgccggtgg taagttatgt aaaaaggtgc ttaacattgt agggccagat gcgcgagggc   4440

atggcaagca atgctattca cttttagagc gtgcttatca gcatattaat aagtgtgaca   4500

atgttgtcac tactttaatt tcggctggta tatttagtgt gcctactgat gtctccctaa   4560

cttacttact tggtgtagtg acaaagaatg tcattcttgt cagtaacaac caggatgatt   4620

ttgatgtgat agagaagtgt caggtgacct ccgttgctgg taccaaagcg ctatcacttc   4680

aattggccaa aaatttgtgc cgtgatgtaa agtttgtgac gaatgcatgt agttcgcttt   4740

ttagtgaatc ttgctttgtc tcaagctatg atgtgttgca ggaagttgaa gcgctgcgac   4800

atgatataca attggatgat gatgctcgtg tctttgtgca ggctaatatg gactgtctgc   4860

ccacagactg gcgactggtt aacaaatttg atagtgttga tggtgttaga accattaagt   4920

attttgaatg cccgggcggg atttttgtat ccagccaggg caaaaagttc ggttatgttc   4980

agaatggttc atttaaggag gcgagtgtta gccaaataag ggctttactc gctaataagg   5040

ttgatgtctt gtgtactgtt gatggtgtta acttccgctc ctgctgcgta gcagagggtg   5100

aagtttttgg caagacatta ggttcagtct tttgtgatgg cataaatgtc accaaagtta   5160

ggtgtagtgc catttacaag ggtaaggttt tctttcagta cagtgatttg tccgaggcag   5220

atcttgtggc tgttaaagat gcctttggtt ttgatgaacc acaactgctg aagtactaca   5280

ctatgcttgg catgtgtaag tggccagtag ttgtttgtgg caattatttt gctttcaagc   5340

agtcaaataa taattgctat ataaatgtgg catgtttaat gctgcaacac ttgagtttaa   5400
```

```
agtttcctaa gtggcaatgg caagaggctt ggaacgagtt ccgctctggt aaaccactaa   5460
ggtttgtgtc cttggtatta gcaaagggca gctttaaatt taatgaacct tctgattcta   5520
tcgattttat gcgtgtggtg ctacgtgaag cagatttgag tggtgccacg tgcaatttgg   5580
aatttgtttg taaatgtggt gtgaagcaag agcagcgcaa aggtgttgac gctgttatgc   5640
attttggtac gttggataaa ggtgatcttg tcaggggtta taatatcgca tgtacgtgcg   5700
gtagtaaact tgtgcattgc acccaattta acgtaccatt tttaatttgc tccaacacac   5760
cagagggtag gaaactgccc gacgatgttg ttgcagctaa tatttttact ggtggtagtg   5820
tgggccatta cacgcatgtg aaatgtaaac ccaagtacca gctttatgat gcttgtaatg   5880
ttaataaggt ttcggaggct aagggtaatt ttaccgattg cctctacctt aaaaatttaa   5940
agcaaacttt ttcgtctgtg ctgacgactt tttatttaga tgatgtaaag tgtgtggagt   6000
ataagccaga tttatcgcag tattactgtg agtctggtaa atattataca aaacccatta   6060
ttaaggccca atttagaaca tttgagaagg ttgatggtgt ctataccaac tttaaattgg   6120
tgggacatag tattgctgaa aaactcaatg ctaagctggg atttgattgt aattctccct   6180
ttgtggagta taaaattaca gagtggccaa cagctactgg agatgtggtg ttggctagtg   6240
atgatttgta tgtaagtcgg tactcaagcg ggtgcattac ttttggtaaa ccggttgtct   6300
ggcttggcca tgaggaagca tcgctgaaat ctctcacata ttttaataga cctagtgtcg   6360
tttgtgaaaa taaatttaat gtgttgcccg ttgatgtcag tgaacccacg gacaaggggc   6420
ctgtgcctgc tgcagtcctt gttaccggcg tccctggagc tgatgcgtca gctggtgccg   6480
gtattgccaa ggagcaaaaa gcctgtgctt ctgctagtgt ggaggatcag gttgttacgg   6540
aggttcgtca agagccatct gtttcagctg ctgatgtcaa agaggttaaa ttgaatggtg   6600
ttaaaaagcc tgttaaggtg gaaggtagtg tggttgttaa tgatcccact agcgaaacca   6660
aagttgttaa aagtttgtct attgttgatg tctatgatat gttcctgaca gggtgtaagt   6720
atgtggtttg gactgctaat gagttgtctc gactagtaaa ttcaccgact gttagggagt   6780
atgtgaagtg gggtatggga aagattgtaa cacccgctaa gttgttgttg ttaagagatg   6840
agaagcaaga gttcgtagcg ccaaaagtag tcaaggcgaa agctattgcc tgctattgtg   6900
ctgtgaagtg gtttctcctc tattgtttta gttggataaa gtttaatact gataataagg   6960
ttatatacac cacagaagta gcttcaaagc ttactttcaa gttgtgctgt ttggccttta   7020
agaatgcctt acagacgttt aattggagcg ttgtgtctag ggcttttttc ctagttgcaa   7080
cggtcttttt attatggttt aactttttgt atgctaatgt tattttgagt gacttctatt   7140
tgcctaatat tgggcctctc cctacgtttg tgggacagat agttgcgtgg tttaagacta   7200
catttggtgt gtcaaccatc tgtgatttct accaggtgac ggatttgggc tatagaagtt   7260
cgttttgtaa tggaagtatg gtatgtgaac tatgcttctc aggttttgat atgctggaca   7320
actatgatgc tataaatgtt gttcaacacg ttgtagatag gcgtttgtcc tttgactata   7380
ttagcctatt taaattagta gttgagcttg taatcggcta ctctctttat actgtgtgct   7440
tctacccact gtttgtcctt attggaatgc agttgttgac cacatggttg cctgaattct   7500
ttatgctgga gactatgcat tggagtgctc gtttgtttgt gtttgttgcc aatatgcttc   7560
cagcttttac gttactgcga ttttacatcg tggtgacagc tatgtataag gtctattgtc   7620
tttgtagaca tgttatgtat ggatgtagta agcctggttg cttgttttgt tataagagaa   7680
accgtagtgt ccgtgttaag tgtagcaccg ttgttggtgg ttcactacgc tattacgatg   7740
```

-continued

```
taatggctaa cggcggcaca ggtttctgta caaagcacca gtggaactgt cttaattgca   7800
attcctggaa accaggcaat acattcataa ctcatgaagc agcggcggac ctctctaagg   7860
agttgaaacg ccctgtgaat ccaacagatt ctgcttatta ctcggtcaca gaggttaagc   7920
aggttggttg ttccatgcgt ttgttctacg agagagatgg acagcgtgtt tatgatgatg   7980
tcaatgctag tttgtttgtg gacatgaatg gtctgctgca ttctaaagtt aaaggtgtgc   8040
ctgaaacgca tgttgtggtt gttgagaatg aagctgataa agctggtttt ctcggcgccg   8100
cagtgtttta tgcacaatcg ctctacagac ctatgttgat ggtggaaaag aaattaataa   8160
ctaccgccaa cactggtttg tctgttagtc gaactatgtt tgacctttat gtagattcat   8220
tgctgaacgt cctcgacgtg gatcgcaaga gtctaacaag ttttgtaaat gctgcgcaca   8280
actctctaaa ggagggtgtt cagcttgaac aagttatgga tacctttatt ggctgtgccc   8340
gacgtaagtg tgctatagat tctgatgttg aaaccaagtc tattaccaag tccgtcatgt   8400
cggcagtaaa tgctggcgtt gattttacgg atgagagttg taataacttg gtgcctacct   8460
atgttaaaag tgacactatc gttgcagccg atttgggtgt tcttattcag aataatgcta   8520
agcatgtaca ggctaatgtt gctaaagccg ctaatgtggc ttgcatttgg tctgtggatg   8580
cttttaacca gctatctgct gacttacagc ataggctgcg aaaagcatgt tcaaaaactg   8640
gcttgaagat taagcttact tataataagc aggaggcaaa tgttcctatt ttaactacac   8700
cgttctctct taaagggggc gctgttttta gtagaatgtt acaatggttg tttgttgcta   8760
atttgatttg tttcattgtg ttgtgggccc ttatgccaac atatgcagtg cacaaatcgg   8820
atatgcagtt gcctttatat gccagtttta aagttataga taatggtgtg ctaagggatg   8880
tgtctgttac tgacgcatgc ttcgcaaaca aatttaatca atttgatcaa tggtatgagt   8940
ctacttttgg tcttgcttat taccgcaact ctaaggcttg tcctgttgtg gttgctgtaa   9000
tagatcaaga cattggccat accttattta atgttcctac cacagtttta agatatggat   9060
ttcatgtgtt gcattttata acccatgcat ttgctactga tagcgtgcag tgttacacgc   9120
cacatatgca aatcccctat gataatttct atgctagtgg ttgcgtgttg tcatccctct   9180
gtactatgct tgcgcatgca gatggaaccc cgcatcctta ttgttataca gggggtgtta   9240
tgcacaatgc ctctctgtat agttctttgg ctcctcatgt ccgttataac ctggctagtt   9300
caaacggtta tatacgtttt cccgaagtgg ttagtgaagg cattgtgcgt gttgtgcgca   9360
ctcgctctat gacctactgc agggttggtt tatgtgagga ggccgaggag ggtatctgct   9420
ttaattttaa tcgttcatgg gtattgaaca acccgtatta tagggccatg cctggaactt   9480
tttgtggtag gaatgctttt gatttaatac atcaagtttt aggaggatta gtgcggccta   9540
ttgatttctt tgccttaacg gcgagttcag tggctggtgc tatccttgca attattgtcg   9600
ttttggcttt ctattattta ataaagctta aacgtgcctt tggtgactac actagtgttg   9660
tggttatcaa tgtaattgtg tggtgtataa attttctgat gctttttgtg tttcaggttt   9720
atcccacatt gtcttgttta tatgcttgtt tttatttcta cacaacgctt tatttccctt   9780
cggagataag tgttgttatg catttgcaat ggcttgtcat gtatggtgct attatgccct   9840
tgtggttttg cattatttac gtggcagtcg ttgtttcaaa ccatgcattg tggttgttct   9900
cttactgccg caaaattggt accgaggttc gtagtgacgg cacatttgag gaaatggccc   9960
ttactacctt tatgattact aaagaatctt attgtaagtt gaaaaattct gtttctgatg  10020
ttgcttttaa caggtacttg agtctttata acaagtatcg ttattttagt ggcaaaatgg  10080
atactgccgc ttatagagag gctgcctgtt cacaactggc aaaggcaatg gaaacattta  10140
```

```
accataataa tggtaatgat gttctctatc agcctccaac cgcctctgtt actacatcat  10200
ttttacagtc tggtatagtg aagatggtgt cgcccacctc taaagtggag ccttgtattg  10260
ttagtgttac ttatggtaac atgacactta atgggttgtg gttggatgat aaagtttatt  10320
gcccaagaca tgttatctgt tcttcagctg acatgacaga ccctgattat cctaatttgc  10380
tttgtagagt gacatcaagt gatttttgtg ttatgtctgg tcgtatgagc cttactgtaa  10440
tgtcttatca aatgcagggc tgccaacttg ttttgactgt tacactgcaa aatcctaaca  10500
cgcctaagta ttccttcggt gttgttaagc ctggtgagac atttactgta ctggctgcat  10560
acaatggcag acctcaagga gccttccatg ttacgcttcg tagtagccat accataaagg  10620
gctcctttct atgtggatcc tgcggttctg taggatatgt tttaactggc gatagtgtac  10680
gatttgttta tatgcatcag ctagagttga gtactggttg tcataccggt actgacttta  10740
gtgggaactt ttatggtccc tatagagatg cgcaagttgt acaattgcct gttcaggatt  10800
atacgcagac tgttaatgtt gtagcttggc tttatgctgc tatttttaac agatgcaact  10860
ggtttgtgca aagtgatagt tgttccctgg aggagtttaa tgtttgggct atgaccaatg  10920
gttttagctc aatcaaagcc gatcttgtct tggatgcgct tgcttctatg acaggcgtta  10980
cagttgaaca ggtgttggcc gctattaaga ggctgcattc tggattccag ggcaaacaaa  11040
ttttaggtag ttgtgtgctt gaagatgagc tgacaccaag tgatgtttat caacaactag  11100
ctggtgtcaa gctacagtca aagcgcacaa gagttataaa aggtacatgt tgctggatat  11160
tggcttcaac gtttttgttc tgtagcatta tctcagcatt tgtaaaatgg actatgttta  11220
tgtatgttac tacccatatg ttgggagtga cattgtgtgc actttgtttt gtaagctttg  11280
ctatgttgtt gatcaagcat aagcatttgt atttaactat gtatattatg cctgtgttat  11340
gcacactgtt ttacaccaac tatttggttg tgtacaaaca gagttttaga ggtctagctt  11400
atgcttggct ttcacacttt gtccctgctg tagattatac atatatggat gaagttttat  11460
atggtgttgt gttgctagta gctatggtgt ttgttaccat gcgtagcata aaccacgacg  11520
tcttttctat tatgttcttg gttggtagac ttgtcagcct ggtatccatg tggtattttg  11580
gagccaattt agaggaagag gtactattgt tcctcacatc cctatttggc acgtacacat  11640
ggactactat gttgtcattg gctaccgcta aggttattgc taaatggttg gctgtgaatg  11700
tcttgtactt cacagacgta ccgcaaatta aattagttct tttgagctac ttgtgtattg  11760
gttatgtgtg ttgttgttat tggggaatct tgtcactcct taatagcatt tttaggatgc  11820
cattgggcgt ctacaattat aaaatctccg ttcaggagtt acgttatatg aatgctaatg  11880
gcttgcgccc acctagaaat agttttgagg ccctgatgct taattttaag ctgttgggaa  11940
ttggtggtgt gccagtcatt gaagtatctc aaattcaatc aagattgacg gatgttaaat  12000
gtgctaatgt tgtgttgctt aattgcctcc agcacttgca tattgcatct aattctaagt  12060
tgtggcagta ttgtagtact ttgcacaatg aaatactggc tacatctgat ttgagcgtgg  12120
ccttcgataa gttggctcag ctcttagttg ttttatttgc taatccagca gcagtggata  12180
gcaagtgcct tgcaagtatt gaagaagtga gcgatgatta cgttcgcgac aatactgtct  12240
tgcaagcctt acagagtgaa tttgttaata tggctagctt cgttgagtat gaacttgcta  12300
agaagaatct agatgaggct aaggctagcg gctctgccaa tcaacagcag attaagcagc  12360
tagagaaggc gtgtaatatt gctaagtcag catatgagcg cgacagagct gttgctcgta  12420
agctggaacg tatggctgat ttagctctta caaacatgta taaagaagct agaattaatg  12480
```

```
ataagaagag taaggtagtg tctgcattgc aaaccatgct ctttagtatg gtgcgtaagc  12540
tagataacca agctcttaat tctattttag ataatgcagt taagggttgt gtacctttga  12600
atgcaatacc atcattgact tcgaacactc tgactataat agtgccagat aagcaggttt  12660
ttgatcaggt tgtggataat gtgtatgtca cctatgctgg gaatgtatgg catatacagt  12720
ttattcaaga tgctgatggt gctgttaaac aattgaatga gatagatgtt aattcaacct  12780
ggcctctagt cattgctgca aataggcata atgaagtgtc tactgttgtt ttgcagaaca  12840
atgagttgat gcctcagaag ttgagaactc aggttgtcaa tagtggctca gatatgaatt  12900
gtaatactcc tacccagtgt tactataata ctactggcac gggtaagatt gtgtatgcta  12960
tcctaagtga ctgtgatggt ctcaagtaca ctaagatagt aaaagaagat ggaaattgtg  13020
ttgttttgga attggatcct ccctgtaagt tttctgttca ggatgtgaag ggccttaaaa  13080
ttaagtacct ttactttgtg aaggggtgta atacactggc tagaggctgg gttgtaggca  13140
ccttatcctc gacagtgaga ttgcaggcgg gtacggcaac tgagtatgcc tccaactctg  13200
caatactgtc gctgtgtgcg ttttctgtag atcctaagaa aacgtacttg gattatataa  13260
aacagggtgg agttcccgtt actaattgtg ttaagatgtt atgtgaccat gctggcactg  13320
gtatggccat tactattaag ccggaggcaa ccactaatca ggattcttat ggtggtgctt  13380
ccgtttgtat atattgccgc tcgcgtgttg aacatccaga tgttgatgga ttgtgcaaat  13440
tacgcggcaa gtttgtccaa gtgcccttag gcataaaaga tcctgtgtca tatgtgttga  13500
cgcatgatgt ttgtcaggtt tgtggctttt ggcgagatgg tagctgttcc tgtgtaggca  13560
caggctccca gtttcagtca aaagacacga actttttaaa cgggttcggg gtacaagtgt  13620
aaatgcccgt cttgtaccct gtgccagtgg cttggacact gatgttcaat taagggcatt  13680
tgacatttgt aatgctaatc gagctggcat tggtttgtat tataaagtga attgctgccg  13740
cttccagcgt gtagatgagg acggcaacaa gttggataag ttctttgttg ttaaaagaac  13800
taatttagaa gtgtataata aggagaaaga atgctatgag ttgacaaaag aatgcggtgt  13860
tgtggctgaa cacgagttct tcacatttga tgtggaggga agtcgggtac cacacatagt  13920
ccgtaaagat ctttcaaagt ttactatgtt agatctttgc tatgcattgc gtcattttga  13980
ccgcaatgat tgttcaactc ttaaggaaat tctacttaca tatgctgagt gtgaagagtc  14040
ctacttccaa aagaaggact ggtatgattt tgttgagaat cctgatataa ttaatgtgta  14100
taaaaagctt ggtcctatat ttaatagagc cctgcttaac actgccaagt ttgcagacgc  14160
attagtggag gcaggcttag taggtgtttt aacacttgat aatcaagatt tatatggtca  14220
atggtatgac tttggagatt ttgtcaagac agtacctggt tgtggtgttg ccgtggcaga  14280
ctcttattat tcatatatga tgccaatgct gactatgtgt catgcgttgg atagtgagtt  14340
gtttgttaat ggtacttata gggagtttga ccttgttcag tatgatttta ctgatttcaa  14400
gctagagctc ttcactaagt attttaagca ttggagtatg acctaccacc cgaacacctg  14460
tgagtgcgag gatgacaggt gcattattca ttgcgccaat tttaatatac tttttagtat  14520
ggtcttacct aagacctgtt ttgggcctct tgttaggcag atatttgtgg atggtgttcc  14580
tttcgttgtg tcgatcggtt accattataa agaattaggt gttgttatga atatggatgt  14640
ggatacacat cgttatcgct tgtctcttaa ggacttgctt ttgtatgctg cagaccctgc  14700
ccttcatgtg gcgtctgcta gtgcactgct tgatttgcgc acatgttgtt ttagcgttgc  14760
agctattaca agtggcgtaa aatttcaaac agttaaacct ggaaatttta atcaggattt  14820
ttatgagttt attttgagta aaggcctgct taaagagggg agctccgttg atttgaagca  14880
```

```
cttcttcttt acgcaggatg gtaatgctgc tattactgat tataattatt acaagtataa  14940
tctacccacc atggtggata ttaagcagtt gttgtttgtt ttagaagttg ttaataagta  15000
ttttgagatc tatgagggtg ggtgtatacc cgcaacacag gtcattgtta ataattatga  15060
taagagtgct ggctatccat ttaataaatt tggaaaggcc aggctctatt atgaggcatt  15120
atcatttgag gagcaggatg aaatttatgc gtataccaaa cgcaatgtcc tgccgaccct  15180
aactcaaatg aatcttaaat atgctattag tgctaagaat agggcccgca ccgttgctgg  15240
tgtctctatt ctcagtacta tgactggcag aatgtttcat caaaagtgtc taaagagtat  15300
agcagctact cgcggtgttc ctgtagttat aggcaccacg aagttctatg gcggttggga  15360
tgatatgtta cgccgcctta ttaaagatgt tgatagtcct gtactcatgg gttgggacta  15420
tcctaaatgt gatcgtgcta tgccaaacat actgcgtatt gttagtagtt tggtgctagc  15480
ccgtaaacat gattcgtgct gttcgcatac ggatagattc tatcgtcttg cgaacgagtg  15540
cgcccaagtt ttgagtgaaa ttgttatgtg tggtggttgt tattatgtta aaccaggtgg  15600
cactagtagt ggggatgcaa ccactgcttt tgctaattct gtgtttaaca tttgtcaagc  15660
tgtttccgcc aatgtatgct cgcttatggc atgcaatgga cacaaaattg aagatttgag  15720
tatacgcgag ttacaaaagc gcctatactc taatgtctat cgtgcggacc atgttgaccc  15780
cgcatttgtt agtgagtatt atgagttttt aaataagcat tttagtatga tgattttgag  15840
tgatgatggt gttgtgtgtt ataattcaga gtttgcgtcc aagggttata ttgctaatat  15900
aagtgccttt caacaggtat tatattatca aaataatgtg tttatgtctg aggccaaatg  15960
ttgggtagaa acagacatcg aaaagggacc gcatgaattt tgttctcaac atacaatgct  16020
agtcaagatg gatggtgatg aagtctacct tccataccct gatccttcga gaatcttagg  16080
agcaggctgt tttgttgatg atttattaaa gactgatagc gttctcttga tagagcgttt  16140
cgtaagtctt gcaattgatg cttatccttt agtataccat gagaacccag agtatcaaaa  16200
tgtgttccgg gtatatttag aatatataaa gaagctgtac aatgatctcg gtaatcagat  16260
cctggacagc tacagtgtta ttttaagtac ttgtgatggt caaaagttta ctgatgagac  16320
cttttacaag aacatgtatt taagaagtgc agtgctgcaa agcgttggtg cctgcgttgt  16380
ctgtagttct caaacatcat tacgttgtgg cagttgcata cgcaagcctt tgctgtgttg  16440
caaatgcgcc tatgatcatg ttatgtccac tgatcataaa tatgtcctga gtgtgtcacc  16500
atatgtgtgt aattcaccgg gatgtgatgt aaatgatgtt accaaattgt atttaggtgg  16560
tatgtcatat tattgtgagg accataaacc acagtattca ttcaaattgg tgatgaatgg  16620
tatggttttt ggtttatata aacaatcttg tactggttcg ccctacatag aggattttaa  16680
taaaatagct agttgcaaat ggacagaagt cgatgattat gtgctagcta atgaatgcac  16740
cgaacgcctt aaattgtttg ccgcagaaac gcagaaggcc acagaagagg cctttaagca  16800
atgttatgcg tcagcaacga tccgtgagat cgtgagcgat cgggagttaa ttttatcttg  16860
ggaaattggt aaagtgagac caccacttaa taaaaattat gtttttactg gctaccattt  16920
tactaataat ggtaagacag ttttaggtga gtatgttttt gataagagtg agttgactaa  16980
tggtgtgtac tatcgcgcca caaccactta taagttatct gtaggtgatg tgttcatttt  17040
aacatcacac gcagtgtcta gtttaagtgc tcctacatta gtaccgcagg agaattatac  17100
tagcattcgt tttgctagtg tttatagtgt gcctgaaacc tttcagaata atgtgcctaa  17160
ttatcagcac attggaatga agcgctattg tactgtacag ggaccgcctg gtactggtaa  17220
```

-continued

```
gtcccatcta gccattgggc tagctgttta ttattgtaca gcgcgcgtgg tgtataccgc  17280
tgctagccat gctgcagttg acgcgctgtg tgaaaaggca cataaatttt taaatattaa  17340
tgactgcacg cgtattgttc ctgcaaaggt gcgtgtagat tgttatgata aatttaaggt  17400
caatgacacc actcgcaagt atgtgtttac tacaataaat gcattacctg agttggtgac  17460
tgacattatt gtcgttgatg aggttagtat gcttaccaac tatgagctgt ctgttattaa  17520
cagccgtgtt agggctaagc attatgtgta tattggagac cctgcgcagt tacctgcacc  17580
acgtgtgcta ctgaataagg gaactctaga acctagatat tttaattccg ttaccaagct  17640
aatgtgttgt ttgggtccag atattttctt gggcacctgt tatagatgcc ctaaggagat  17700
tgtggatacg gtgtcagcct tggtttataa taataagctg aaggctaaaa atgataatag  17760
ctccatgtgc tttaaggttt attataaggg ccagactaca catgagagtt ctagtgctgt  17820
taatatgcag caaatacatt taattagtaa gtttttaaag gcaaacccca gttggagtaa  17880
cgccgtattt attagtcctt ataatagtca gaactatgtt gctaagagag tcttgggatt  17940
acaaacccag acagtagact cagcgcaggg ttctgaatat gattttgtta tttattcaca  18000
gactgcggaa acagcgcatt ctgtcaatgt aaatagattc aatgttgcta ttacacgtgc  18060
taagaagggt attctctgtg tcatgagtag tatgcaatta tttgagtctc ttaattttac  18120
tacactgacg ttggataaga ttaacaatcc acgattacag tgtactacaa atttgtttaa  18180
ggattgtagc aggagctatg taggatatca cccagcccat gcaccatcct tttggcagt  18240
tgatgacaaa tataaggtag gcggtgattt agccgtttgc cttaatgttg ctgattctgc  18300
tgtcacttat tcgcggctta tatcactcat gggattcaag cttgacttga cccttgatgg  18360
ttattgtaag ctgtttataa ctagagatga agctatcaaa cgtgttagag cctgggttgg  18420
cttcgatgca gaaggtgccc atgcgatacg tgatagcatt gggacaaatt tcccattaca  18480
attaggcttt tcgactggaa ttgattttgt tgtcgaagcc actggaatgt ttgctgagag  18540
agatggttat gtctttaaaa aggcagccgc acgagctcct cctggcgaac aatttaaaca  18600
ccttatccca cttatgtcaa gagggcagaa atgggatgtg gttcgaatta gaatagtaca  18660
aatgttgtca gaccacctag cggatttggc agacagtgtt gtacttgtga cgtgggctgc  18720
cagctttgag ctcacatgtt tgcgatattt cgctaaagtt ggaagagaag ttgtgtgtag  18780
tgtctgcacc aagcgtgcga catgttttaa ttctagaact ggatactatg gatgctggcg  18840
acatagttat tcctgtgatt acctgtacaa cccactaata gttgacattc aacagtgggg  18900
atatacagga tctttaacta gcaatcatga tcctatttgc agcgtgcata agggtgctca  18960
tgttgcatca tctgatgcta tcatgacccg gtgtctagct gttcatgatt gcttttgtaa  19020
gtctgttaat tggaatttag aataccccat tatttcaaat gaggtcagtg ttaatacctc  19080
ctgcaggtta ttgcagcgcg taatgtttag ggctgcgatg ctatgcaata ggtatgatgt  19140
gtgttatgac attggcaacc ctaaaggtct tgcctgtgtc aaaggatatg attttaagtt  19200
ttatgatgcc tcccctgttg ttaagtctgt taaacagttt gtttataaat acgaggcaca  19260
taaagatcaa tttttagatg gtttgtgtat gttttggaac tgcaatgtgg ataagtatcc  19320
agcgaatgca gttgtgtgta ggtttgacac gcgtgtgttg aacaaattaa atctccctgg  19380
ctgtaatggt ggcagtttgt atgttaacaa acatgcattc cacaccagtc cctttacccg  19440
ggctgccttc gagaatttga agcctatgcc tttcttttat tattcagata cgccctgtgt  19500
gtatatggaa ggcatggaat ctaagcaggt cgattatgtc ccattgagaa gcgctacatg  19560
catcacaaga tgcaatttag gtggcgctgt ttgtttaaaa catgctgagg agtatcgtga  19620
```

-continued

```
gtaccttgag tcttacaata cggcaaccac agcgggtttt actttttggg tctataagac  19680
ttttgatttt tataaccttt ggaatacttt tactaggctc caaagtttag aaaatgtagt  19740
gtataatttg gtcaatgctg gacactttga tggccgggcg ggtgaactgc cttgtgctgt  19800
tataggtgag aaagtcattg ccaagattca aaatgaggat gtcgtggtct ttaaaaataa  19860
cacgccattc cccactaatg tggccgtcga attatttgct aagcgcagta ttcggcccca  19920
ccccgagctt aagctcttta gaaatttgaa tattgacgtg tgctggagtc acgtcctttg  19980
ggattatgct aaggatagtg tgttttgcag ttcgacgtat aaggtctgca aatacacaga  20040
tttacagtgc attgaaagct tgaatgtact ttttgatggt cgtgataatg gtgctcttga  20100
agcttttaag aagtgccgga atggcgtcta cattaacacg acaaaaatta aaagtctgtc  20160
gatgattaaa ggcccacaac gtgccgattt gaatggcgta gttgtggaga aagttggaga  20220
ttctgatgtg gaattttggt ttgctgtgcg taaagacggt gacgatgtta tcttcagccg  20280
tacagggagc cttgaaccga gccattaccg gagcccacaa ggtaatccgg gtggtaatcg  20340
cgtgggtgat ctcagcggta atgaagctct agcgcgtggc actatcttta ctcaaagcag  20400
attattatct tctttcacac ctcgatcaga gatggagaaa gattttatgg atttagatga  20460
tgatgtgttc attgcaaaat atagtttaca ggactacgcg tttgaagccg ttgtttatgg  20520
tagttttaac cagaagatta ttggaggttt gcatttgctt attggcttag cccgtaggca  20580
gcaaaaatcc aatctggtaa ttcaagagtt cgtgacatac gactctagca ttcattcgta  20640
ctttatcact gacgagaaca gtggtagtag taagagtgtg tgcactgtta ttgatttatt  20700
gttagatgat tttgtggaca ttgtaaagtc cctgaatcta aagtgtgtga gtaaggttgt  20760
taatgttaat gttgatttta aagatttcca gtttatgttg tggtgcaatg aggagaaggt  20820
catgactttc tatcctcgtt tgcaggctgc tgctgactgg aaacctggtt atgttatgcc  20880
tgtcttatat aagtatttgg aatcgcctct ggaaagagta aacctctgga attatggcaa  20940
gccgattact ttacctacag gatgtatgat gaatgttgct aagtatactc aattatgtca  21000
atatttgagc actacaacat tagcagttcc ggctaatatg cgtgtcttac accttggtgc  21060
cggttcggat aagggtgttg cccctgggtc tgcagttctt aggcagtggc taccagcggg  21120
aagtattctt gtagataatg atgtgaatcc atttgtgagt gacagtgtcg cctcatatta  21180
tggaaattgt ataaccttac cctttgattg tcagtgggat ctgataattt ctgatatgta  21240
cgaccctctt actaagaaca ttggggagta caacgtgagt aaagatggat tctttactta  21300
cctctgtcat ttaattcgtg acaagttggc tctgggtggc agtgttgcca taaaaataac  21360
agagttttct tggaacgctg agttatatag tttaatgggg aagtttgcgt tctggacaat  21420
cttttgcacc aacgtaaacg cctcttcaag tgaaggattt ttgattggca taaattggtt  21480
gaataagacc cgtaccgaaa ttgacggtaa aaccatgcat gccaattatc tgttttggag  21540
aaatagtaca atgtggaatg gaggggctta cagtctcttt gacatgagta agttcccttt  21600
gaaagcggct ggtacggctg ttgttagcct taaaccagac caaataaatg acttagtcct  21660
ctccttgatt gagaagggca agttattagt gcgtgataca cgcaaagaag tttttgttgg  21720
cgatagccta gtaaatgtca aataaatcta tacttgtcgt ggctgtgaaa atggcctttg  21780
ctgacaagcc taatcatttc ataaactttc ccctggccca atttagtggc tttatgggta  21840
agtatttaaa gctacagtct caacttgtgg aaatgggttt agactgtaaa ttacagaagg  21900
caccacatgt tagtattacc ctgcttgata ttaaagcaga ccaatacaaa caggtggaat  21960
```

-continued

```
ttgcaataca agaaataata gatgatctgg cggcatatga gggagatatt gtctttgaca  22020
accctcacat gcttggcaga tgccttgttc ttgatgttag aggatttgaa gagttgcatg  22080
aagatattgt tgaaattctc cgcagaaggg gttgcacggc agatcaatcc agacactgga  22140
ttccgcactg cactgtggcc caatttgacg aagaaagaga aacaaaagga atgcaattct  22200
atcataaaga acccttctac ctcaagcata acaacctatt aacggatgct gggcttgagc  22260
tcgtgaagat aggttcttcc aaaatagatg ggttttattg tagtgaactg agtgtttggt  22320
gtggtgagag gctttgttat aagcctccaa cacccaaatt cagtgatata tttggctatt  22380
gctgcataga taaaatacgt ggtgatttag aaataggaga cctaccgcag gatgatgagg  22440
aagcgtgggc cgagctaagt taccactatc aaagaaacac ctacttcttc agacatgtgc  22500
acgataatag catctatttt cgtaccgtgt gtagaatgaa gggttgtatg tgttgatttg  22560
tttttacact attagtgtaa taagcttatt attttgttga aaagggcggg atgtgcatag  22620
ctatggctcc tctcacactg cttttgctga tttgatgtca gctggtgttt gggttcaatg  22680
aacctcttaa catcgtttca catttaaatg atgactggtt tctatttggt gacagtcggt  22740
ccgactgtac ctatgtagaa aataacggtc atcctaaatt agattggctt gacctcgacc  22800
caaagttgtg taattcagga aagatttccg caaagagtgg taactctctc tttaggagtt  22860
ttcacttcac tgatttttac aattatacgg gtgagggaga ccaaattgta ttttatgaag  22920
gagttaattt tagtcccagc catggcttta aatgcctggc tcatggagat aataaaagat  22980
ggatgggcaa taaagctcga ttttatgccc gagtgtatga gaagatggcc caatatagga  23040
gcctatcgtt tgttaatgtg tcttatgcct atggaggtaa tgcaaagccc gcctccattt  23100
gcaaagacaa tactttaaca ctcaataacc ccaccttcat atcgaaggag tctaattatg  23160
ttgattatta ctatgagagt gaggctaatt tcacactaga aggttgtgat gaatttatag  23220
taccgctctg tggttttaat ggccattcca agggcagctc ttcggatgct gccaataaat  23280
attatactga ctctcagagt tactataata tggatattgg tgtcttatat gggttcaatt  23340
cgaccttgga tgttggcaac actgctaagg atccgggtct tgatctcact tgtaggtatc  23400
ttgcattgac tcctggtaat tataaggctg tgtccttaga gtatttgtta agcttaccct  23460
caaaggctat ttgcctccat aagacaaagc gctttatgcc tgtgcaggta gttgactcaa  23520
ggtggagtag catccgccag tcagacaata tgaccgctgc agcctgtcag ctgccatatt  23580
gtttctttcg caacacatct gcgaattata gtggtggcac acatgatgcg caccatggtg  23640
attttcattt caggcagtta ttgtctggtt tgttatataa tgtttcctgt attgcccagc  23700
agggtgcatt tctttataat aatgttagtt cctcttggcc agcctatggg tacggtcatt  23760
gtccaacggc agctaacatt ggttatatgg cacctgtttg tatctatgac cctctcccgg  23820
tcatactgct aggtgtgtta ttgggtatag ctgtgttgat tattgtgttt ttgatgtttt  23880
attttatgac ggatagcggt gttagattgc atgaggcata atctaaacat gctgttcgtg  23940
tttattctat ttttgccctc ttgcctaggg tatattggtg attttagatg tatccagctt  24000
gtgaattcaa acggtgctaa tgttagtgct ccaagcatta gcactgagac cgttgaagtt  24060
tcacaaggcc tggggacata ttatgtgtta gatcgagttt atttaaatgc cacattattg  24120
cttactggtt actacccggt cgatggttct aagtttagaa acctcgctct tacgggaact  24180
aactcagtta gcttgtcgtg gtttcaacca ccctatttaa gtcagtttaa tgatggcata  24240
tttgcgaagg tgcagaacct taagacaagt acgccatcag gtgcaactgc atattttcct  24300
actatagtta taggtagttt gtttggctat acttcctata ccgttgtaat agagccatat  24360
```

```
aatggtgtta taatggcctc agtgtgccag tataccattt gtcagttacc ttacactgat  24420
tgtaagccta acactaatgg taataaatta atagggtttt ggcacacgga tgtaaaaccc  24480
ccaatttgtg tgttaaagcg aaatttcacg cttaatgtta atgctgatgc attttatttt  24540
catttttacc aacatggtgg tactttttat gcgtactatg cggataaacc ctccgctact  24600
acgtttttgt ttagtgtata tattggcgat attttaacac agtattatgt gttacctttc  24660
atctgcaacc caacagctgg tagcactttt gctccgcgct attgggttac acctttggtt  24720
aagcgccaat atttgtttaa tttcaaccag aagggtgtca ttactagtgc tgttgattgt  24780
gctagtagtt ataccagtga aataaaatgt aagacccaga gcatgttacc tagcactggt  24840
gtctatgagt tatccggtta tacggtccaa ccagttggag ttgtataccg gcgtgttgct  24900
aacctcccag cttgtaatat agaggagtgg cttactgcta ggtcagtccc ctcccctctc  24960
aactgggagc gtaagacttt tcagaattgt aattttaatt taagcagcct gttacgttat  25020
gttcaggctg agagtttgtt ttgtaataat atcgatgctt ccaaagtgta tggcaggtgc  25080
tttggtagta tttcagttga taagtttgct gtaccccgaa gtaggcaagt tgatttacag  25140
cttggtaact ctggatttct gcagactgct aattataaga ttgatacagc tgccacttcg  25200
tgtcagctgc attacacctt gcctaagaat aatgtcacca taaacaacca taacccctcg  25260
tcttggaata ggaggtatgg ctttaatgat gctggcgtct ttggcaaaaa ccaacatgac  25320
gttgtttacg ctcagcaatg ttttactgta agatctagtt attgcccgtg tgctcaaccg  25380
gacatagtta gcccttgcac tactcagact aagcctaagt ctgcttttgt taatgtgggt  25440
gaccattgtg aaggcttagg tgttttagaa gataattgtg gcaatgctga tccacataag  25500
ggttgtatct gtgccaacaa ttcatttatt ggatggtcac atgatacctg ccttgttaat  25560
gatcgctgcc aaatttttgc taatatattg ttaaatggca ttaatagtgg taccacatgt  25620
tccacagatt tgcagttgcc taatactgaa gtggttactg gcatttgtgt caaatatgac  25680
ctctacggta ttactggaca aggtgttttt aaagaggtta aggctgacta ttataatagc  25740
tggcaaaccc ttctgtatga tgttaatggt aatttgaatg gttttcgtga tcttaccact  25800
aacaagactt atacgataag gagctgttat agtggccgtg tttctgctgc atttcataaa  25860
gatgcacccg aaccggctct gctctatcgt aatataaatt gtagctatgt ttttagcaat  25920
aatatttccc gtgaggagaa cccacttaat tactttgata gttatttggg ttgtgttgtt  25980
aatgctgata accgcacgga tgaggcgctt cctaattgtg atctccgtat gggtgctggc  26040
ttatgcgttg attattcaaa atcacgcagg gctcaccgat cagtttctac tggctatcgg  26100
ttaactacat ttgagccata cactccgatg ttagttaatg atagtgtcca atccgttgat  26160
ggattatatg agatgcaaat accaaccaat tttactattg ggcaccatga ggagttcatt  26220
caaactagat ctccaaaggt gactatagat tgtgctgcat ttgtctgtgg tgataacact  26280
gcatgcaggc agcagttggt tgagtatggc tctttctgtg ttaatgttaa tgccattctt  26340
aatgaggtta ataacctctt ggataaatatg caactacaag ttgctagtgc attaatgcag  26400
ggtgttacta taagctcgag actgccagac ggcatctcag gccctataga tgacattaat  26460
tttagtcctc tacttggatg cataggttca acatgtgctg aagacggcaa tggacctagt  26520
gcaatccgag ggcgttctgc tatagaggat ttgttatttg acaaggtcaa attatctgat  26580
gttggctttg tcgaggctta taataattgc accggtggtc aagaagttcg tgacctcctt  26640
tgtgtacaat cttttaacgg catcaaagta ttacctcctg tgttgtcaga gagtcagatc  26700
```

```
tctggctaca caaccggtgc tactgcggca gctatgttcc caccgtggtc agcagctgcc  26760
ggtgtgccat ttagtttaag tgttcaatat agaattaatg gtttaggtgt cactatgaat  26820
gtgcttagtg agaaccaaaa gatgattgct agtgctttta acaatgcgct gggtgctatc  26880
caggatgggt ttgatgcaac caattctgct ttaggtaaga tccagtccgt tgttaatgca  26940
aatgctgaag cactcaataa cttactaaat caactttcta acaggtttgg tgctattagt  27000
gcttctttac aagaaattct aactcggctt gaggctgtag aagcaaaagc ccagatagat  27060
cgtcttatta atggcaggtt aactgcactt aatgcgtata tatccaagca acttagtgat  27120
agtacgctta ttaaagttag tgctgctcag gccatagaaa aggtcaatga gtgcgttaag  27180
agccaaacca cgcgtattaa tttctgtggc aatggtaatc atatattatc tcttgtccag  27240
aatgcgcctt atggcttata ttttatacac ttcagctatg tgccaatatc ctttacaacc  27300
gcaaatgtga gtcctggact ttgcatttct ggtgatagag gattagcacc taaagctgga  27360
tattttgttc aagatgatgg agaatggaag ttcacaggca gttcatatta ctaccctgaa  27420
cccattacag ataaaaacag tgtcattatg agtagttgcg cagtaaacta cacaaaggca  27480
cctgaagttt tcttgaacac ttcaatacct aatccacccg actttaagga ggagttagat  27540
aaatggttta agaatcagac gtctattgcg cctgatttat ctctcgattt cgagaagtta  27600
aatgttactt tgctggacct gacgtatgag atgaacagga ttcaggatgc aattaagaag  27660
ttaaatgaga gctacatcaa cctcaaggaa gttggcacat atgaaatgta tgtgaaatgg  27720
ccttggtatg tttggttgct aattggatta gctggtgtag ctgtttgtgt gttgttattc  27780
tttatatgtt gctgcacagg ttgtggctca tgttgtttta agaagtgtgg aaattgttgt  27840
gatgagtatg gaggacacca ggacagtatt gtgatacata atatttcctc tcatgaggat  27900
tgactatcac agcccctgca ggaaagacag aaaatctaaa caatttatag cattctcatt  27960
gctacctggc cccgtaagag gcagtcatag ctatggccgt gttggtccta aggctacatt  28020
ggctgctgtc tttattggtc catttattgt agcatgtatg ctaggcattg gcctagttta  28080
tttattgcaa ttgcaagttc aaatttttca tgttaaggat accatacgtg tgactggcaa  28140
gccagccact gtgtcttata ctacaagtac accagtaaca ccgagcgcga cgacgctcga  28200
tggtactacg tatactttaa ttagacccac tagctcttat acaagagttt atcttggtac  28260
tccaagaggt tttgattata gtacatttgg gcctaagacc ctagattatg ttactaatct  28320
aaacctcatc ttaattctgg tcgtccatat acttttaagg cattgtccag gcatatgaga  28380
ccaacagcca catggatttg gcatgtgagt gatgcatggt tacgccgcac gcgggacttt  28440
ggtgtcattc gcctagaaga tttttgtttt caatttaatt atagccaacc ccgagttggt  28500
tattgtagag ttcctttaaa ggcttggtgt agcaaccagg gtaaatttgc agcgcagttt  28560
accctaaaaa gttgcgaaaa accaggtcac gaaaaattta ttactagctt cacggcctac  28620
ggcagaactg tccaacaggc cgttagcaag ttagtagaag aagctgttga ttttattctt  28680
tttagggcca cgcagctcga aagaaatgtt taatttattc cttacagaca cagtatggta  28740
tgtggggcag attattttta tattcgcagt gtgtttgatg gtcaccataa ttgtggttgc  28800
cttccttgcg tctatcaaac tttgtattca actttgcggt ttatgtaata ctttggtgct  28860
gtccccttct atttatttgt atgataggag taagcagctt tataagtatt ataatgaaga  28920
aatgagactg cccctattag aggtggatga tatctaatcc aaacattatg agtagtacta  28980
ctcaggcccc agagcccgtc tatcaatgga cggccgacga ggcagttcaa ttccttaagg  29040
aatggaactt ctcgttgggc attatactac tctttattac tatcatacta cagttcggtt  29100
```

-continued

```
acacgagccg tagcatgttt atttatgttg tgaaaatgat aatcttgtgg ttaatgtggc  29160
cactgactat tgttttgtgt attttcaatt gcgtgtatgc gctaaataat gtgtatcttg  29220
gattttctat agtgtttact atagtgtcca ttgtaatctg gattatgtat tttgttaata  29280
gcataaggtt gtttatcagg actggtagct ggtggagctt caaccccgaa acaaacaacc  29340
ttatgtgtat agatatgaaa ggtaccgtgt atgttagacc cattattgag gattaccata  29400
cactaacagc cactattatt cgtggccacc tctacatgca aggtgttaag ctaggcaccg  29460
gtttctcttt gtctgacttg cccgcttatg ttacagttgc taaggtgtca cacctttgca  29520
cttataagcg cgcattctta gacaaggtag acggtgttag cggttttgct gtttatgtga  29580
agtccaaggt cggaaattac cgactgccct caaacaaacc gagtggcgcg gacaccgcat  29640
tgttgagaac ctaatctaaa ctttaaggat gtcttttgtt cctgggcaag aaaatgccgg  29700
tggcagaagc tcctctgtaa accgcgctgg taatggaatc ctcaagaaga ccacttgggc  29760
tgaccaaacc gagcgtggac caaataatca aaatagaggc agaaggaatc agccaaagca  29820
gactgcaact actcaaccca actccgggag tgtggttccc cattactcct ggttttctgg  29880
cattacccag ttccaaaagg gaaaggagtt tcagtttgca gaaggacaag gagtgcctat  29940
tgccaatgga atccccgctt cagagcaaaa gggatattgg tatagacaca accgccgttc  30000
ttttaaaaca cctgatgggc agcagaagca attactgccc agatggtatt tttactatct  30060
tggcacaggg ccccatgctg gagccagtta tggagacagc attgaaggtg tcttctgggt  30120
tgcaaacagc caagcggaca ccaatacccg ctctgatatt gtcgaaaggg acccaagcag  30180
tcatgaggct attcctacta ggtttgcgcc cggcacggta ttgcctcagg gcttttatgt  30240
tgaaggctct ggaaggtctg cacctgctag ccgatctggt tcgcggtcac aatcccgtgg  30300
gccaaataat cgcgctagaa gcagttccaa ccagcgccag cctgcctcta ctgtaaaacc  30360
tgatatggcc gaagaaattg ctgctcttgt tttggctaag ctcggtaaag atgccggcca  30420
gcccaagcaa gtaacgaagc aaagtgccaa agaagtcagg cagaaaattt taaacaagcc  30480
tcgccaaaag aggactccaa acaagcagtg cccagtgcag cagtgttttg gaaagagagg  30540
ccccaatcag aattttggag gctctgaaat gttaaaactt ggaactagtg atccacagtt  30600
ccccattctt gcagagttgg ctccaacagt tggtgccttc ttctttggat ctaaattaga  30660
attggtcaaa aagaattctg gtggtgctga tgaacccacc aaagatgtgt atgagctgca  30720
atattcaggt gcagttagat ttgatagtac tctacctggt tttgagacta tcatgaaagt  30780
gttgaatgag aatttgaatg cctaccagaa ggatggtggt gcagatgtgg tgagcccaaa  30840
gccccaaaga aaagggcgta gacaggctca ggaaaagaaa gatgaagtag ataatgtaag  30900
cgttgcaaag cccaaaagct ctgtgcagcg aaatgtaagt agagaattaa ccccagagga  30960
tagaagtctg ttggctcaga tccttgatga tggcgtagtg ccagatgggt tagaagatga  31020
ctctaatgtg taaagagaat gaatcctatg tcggcgctcg gtggtaaccc ctcgcgagaa  31080
agtcgggata ggacactctc tatcagaatg gatgtcttgc tgtcataaca gatagagaag  31140
gttgtggcag accctgtatc aattagttga aagagattgc aaaatagaga atgtgtgaga  31200
gaagttagca aggtcctacg tctaaccata agaacggcga taggcgcccc ctgggaagag  31260
ctcacatcag ggtactattc ctgcaatgcc ctagtaaatg aatgaagttg atcatggcca  31320
attggaagaa tcacaaaaaa aaaaaaaaaa aaaaaaaaaa aaaaa                  31365
```